(12) United States Patent
Manke et al.

(10) Patent No.: US 9,833,575 B2
(45) Date of Patent: Dec. 5, 2017

(54) SYRINGE WITH PLUNGER ROD HAVING A FLEXIBLE PORTION

(71) Applicant: Becton Dickinson France, S.A.S., Le Pont-de-Claix (FR)

(72) Inventors: Darrin Scott Manke, North Andover, MA (US); Christopher Labak, Brookline, NH (US); Joseph Omer St. Cyr, Salem, NH (US); David Robert Schiff, Highland Park, NJ (US); Mathieu Dominic Turpault, Pennington, NJ (US); Antonio Gatta, Philadelphia, PA (US); John Depler Coleman, Philadelphia, PA (US)

(73) Assignee: Becton Dickinson France, S.A.S., Le Pont-de-Claix (FR)

( * ) Notice: Subject to any disclaimer, the term of this patent is extended or adjusted under 35 U.S.C. 154(b) by 0 days.

(21) Appl. No.: 15/040,416

(22) Filed: Feb. 10, 2016

(65) Prior Publication Data

US 2016/0158452 A1    Jun. 9, 2016

Related U.S. Application Data

(63) Continuation of application No. 13/622,388, filed on Sep. 19, 2012, now Pat. No. 9,289,556.

(Continued)

(51) Int. Cl.
*A61M 5/315*        (2006.01)
*A61M 5/00*         (2006.01)
(Continued)

(52) U.S. Cl.
CPC .... *A61M 5/31513* (2013.01); *A61M 5/31511* (2013.01); *A61M 5/002* (2013.01);
(Continued)

(58) Field of Classification Search
CPC .............. A61M 5/31511; A61M 5/002; A61M 5/31515; A61M 2005/3106; A61M 5/5086; A61M 2005/31518; A61M 2005/3104
(Continued)

(56) References Cited

U.S. PATENT DOCUMENTS 3,035,691 A * 5/1962 Kai Rasmussen .. A61M 25/002
                                              206/364
3,157,277 A    11/1964 Sorenson
(Continued)

FOREIGN PATENT DOCUMENTS

DE    100 48 220 A1    5/2001
WO       98/01173 A1    1/1998
WO    2007/075677 A2    7/2007

*Primary Examiner* — Manuel Mendez
(74) *Attorney, Agent, or Firm* — The Webb Law Firm

(57) ABSTRACT

A syringe assembly including a plunger rod having a first end, a second end, and a rod portion extending therebetween, wherein at least a portion of the rod portion is flexible is disclosed. The flexible portion of the rod portion allows a stopper to be moved between a first position and a second position within a syringe barrel while the overall length of the syringe assembly remains the same throughout the movement between the first position and the second position. In another embodiment, a syringe assembly including a restraining member adapted to communicate with the flexible portion of the rod portion such that movement of the first end of the plunger rod in a first direction actuates movement of the second end of the plunger rod in a second direction different than the first direction is disclosed.

19 Claims, 17 Drawing Sheets

Related U.S. Application Data

(60) Provisional application No. 61/541,406, filed on Sep. 30, 2011.

(51) Int. Cl.
*A61M 5/50* (2006.01)
*A61M 5/31* (2006.01)

(52) U.S. Cl.
CPC ....... *A61M 5/31515* (2013.01); *A61M 5/5086* (2013.01); *A61M 2005/3104* (2013.01); *A61M 2005/3106* (2013.01); *A61M 2005/31518* (2013.01)

(58) Field of Classification Search
USPC ....... 604/187, 218, 221, 222, 223, 224, 227, 604/228, 233
See application file for complete search history.

(56) References Cited

U.S. PATENT DOCUMENTS

| | | | | |
|---|---|---|---|---|
| 3,786,811 A * | 1/1974 | Holbrook | ............ | A61M 5/3129 604/218 |
| 4,493,704 A * | 1/1985 | Beard | ................. | A61M 5/1452 604/154 |
| 4,599,082 A * | 7/1986 | Grimard | ................ | A61M 5/284 215/355 |
| 4,613,326 A * | 9/1986 | Szwarc | ................ | A61M 5/284 604/218 |
| 5,064,098 A * | 11/1991 | Hutter, III | ......... | B05C 17/00553 222/137 |
| 5,496,285 A | 3/1996 | Schumacher et al. | | |
| 5,637,095 A * | 6/1997 | Nason | ............... | A61M 5/14244 604/135 |
| 5,957,889 A * | 9/1999 | Poulsen | ............ | A61M 5/14566 604/131 |
| 6,045,537 A * | 4/2000 | Klitmose | ................ | A61M 5/24 604/224 |
| 6,245,046 B1 * | 6/2001 | Sibbitt | .................. | A61M 5/284 604/191 |
| 6,537,251 B2 * | 3/2003 | Klitmose | ........... | A61M 5/14566 604/131 |
| 7,220,248 B2 * | 5/2007 | Mernoe | ............. | A61M 5/14244 604/218 |
| 7,985,201 B2 * | 7/2011 | Langley | ................. | A61M 5/20 604/131 |
| 8,517,991 B2 * | 8/2013 | Clemente | .......... | A61M 5/14244 604/131 |
| 9,289,556 B2 * | 3/2016 | Manke | ............. | A61M 5/31511 |
| 2010/0249706 A1 * | 9/2010 | Clemente | .......... | A61M 5/14244 604/154 |
| 2012/0253292 A1 * | 10/2012 | Ivosevic | ........... | A61M 5/31513 604/222 |

* cited by examiner

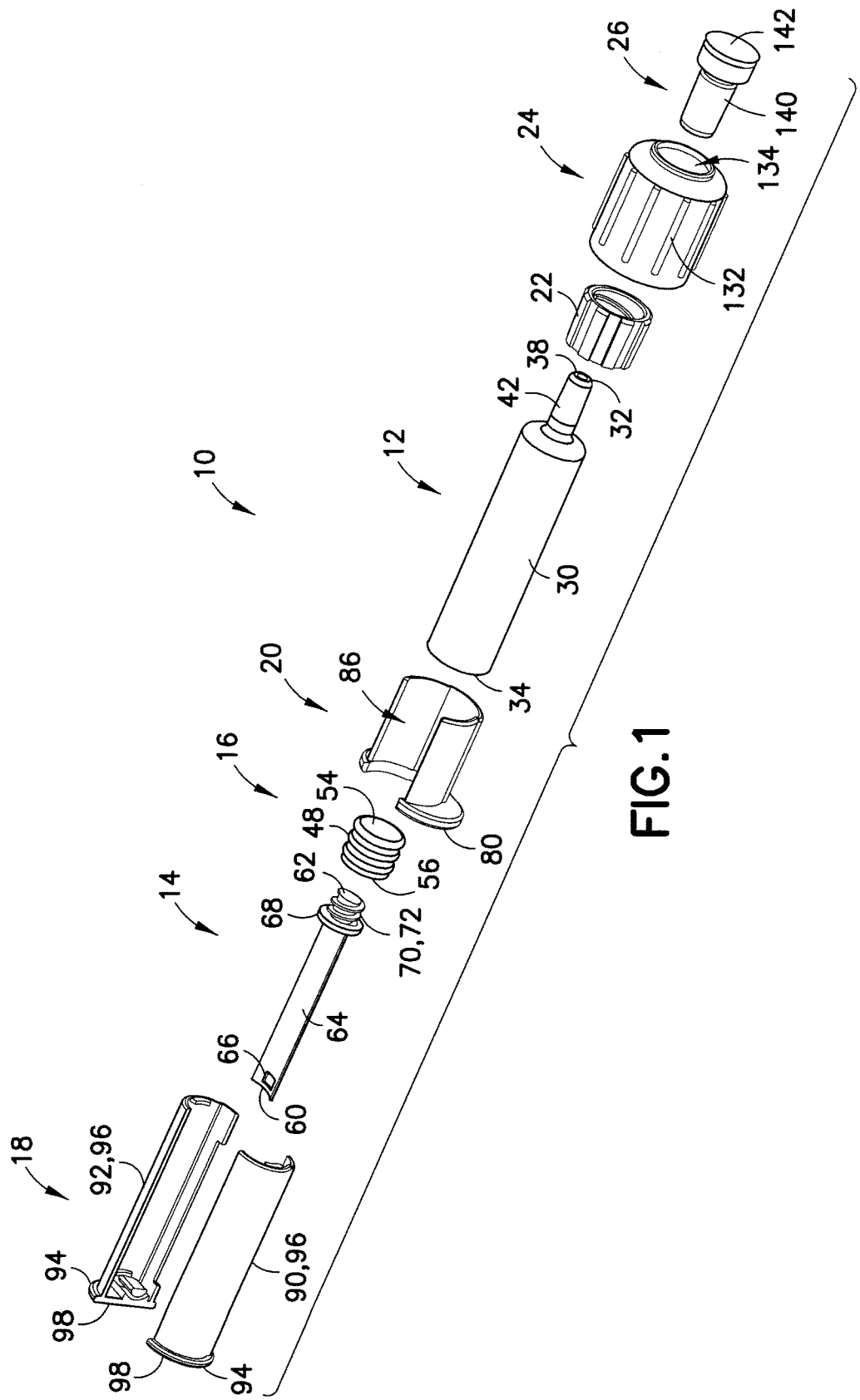

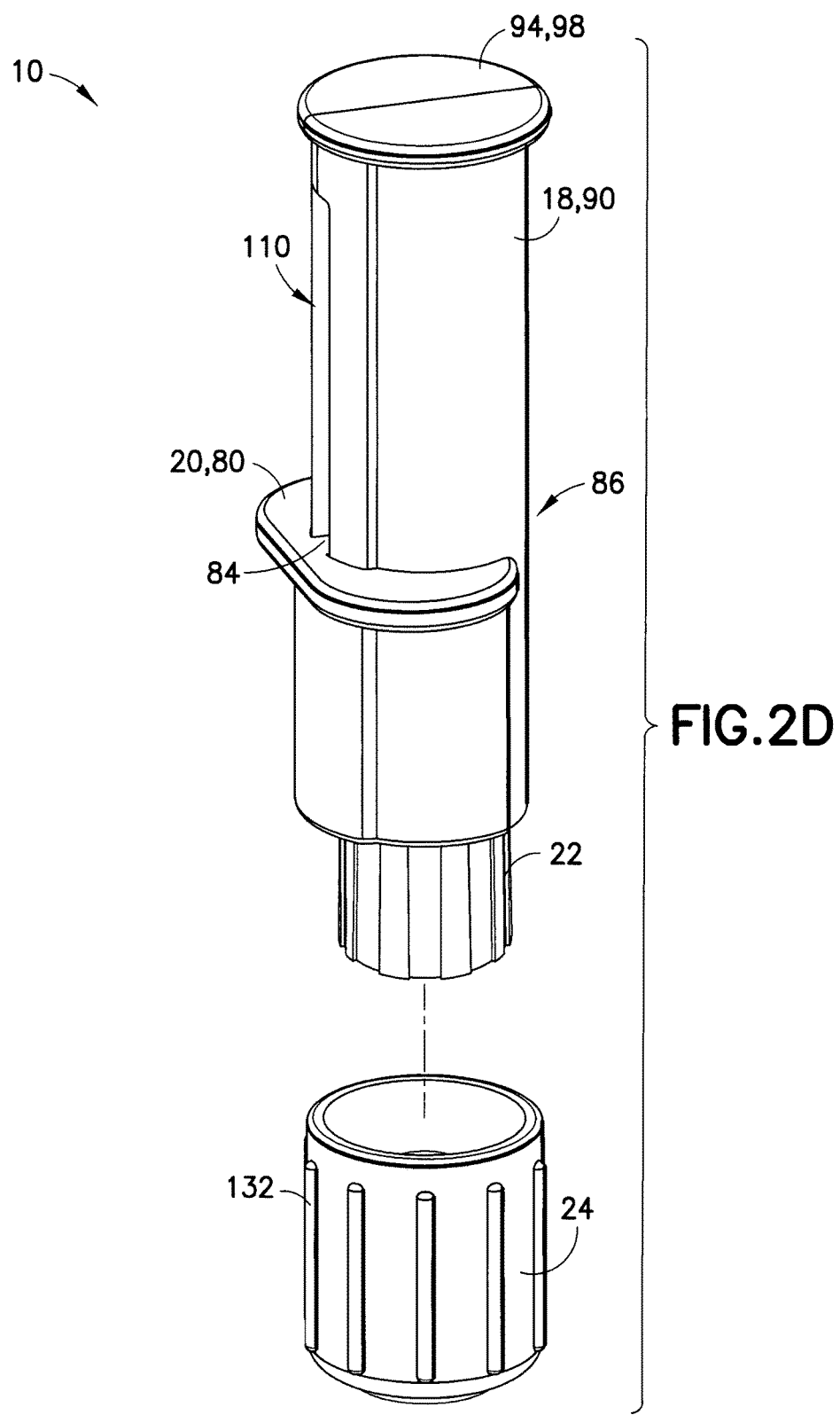

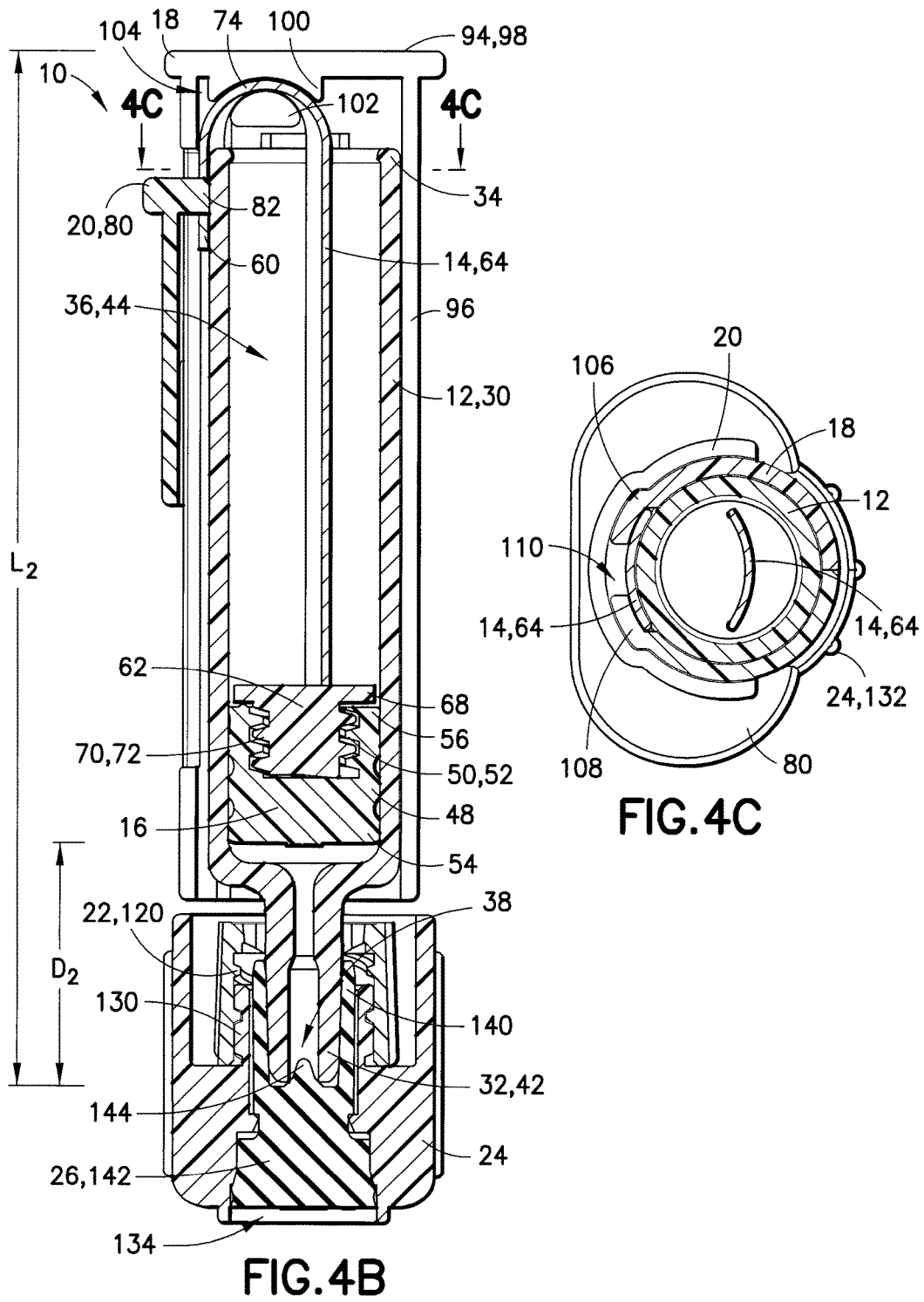

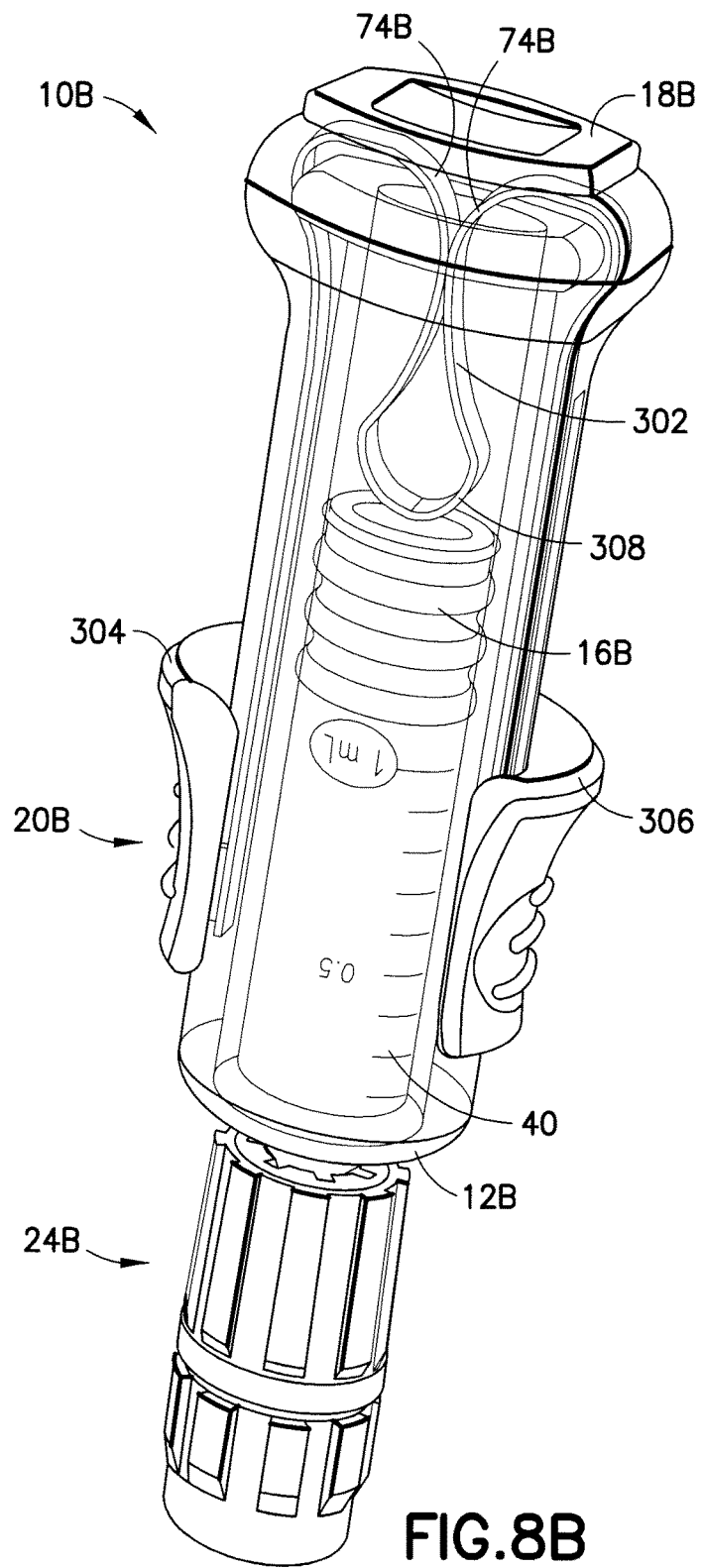

SYRINGE WITH PLUNGER ROD HAVING A FLEXIBLE PORTION

CROSS-REFERENCE TO RELATED APPLICATION

This application claims priority to U.S. application Ser. No. 13/622,388, filed Sep. 19, 2012, entitled "Syringe with Plunger Rod Having a Flexible Portion", which claims priority to U.S. Provisional Application No. 61/541,406 filed Sep. 30, 2011, the entire disclosures of each of which are hereby incorporated by reference.

BACKGROUND OF THE INVENTION

1. Field of the Disclosure

The present disclosure relates generally to a syringe assembly adapted for delivery of a fluid and/or collection of a fluid. More particularly, the present disclosure relates to a syringe assembly including a plunger rod having a flexible portion in which movement of a first end of the plunger rod in a first direction causes movement of the stopper in a different direction.

2. Description of the Related Art

Syringe assemblies, and in particular hypodermic syringes, are well known in the medical field for dispensing fluids, such as medications. A conventional syringe typically includes a syringe barrel with an opening at one end and a plunger mechanism disposed through the opposite end. The plunger typically includes a rigid plunger rod having a linear longitudinal axis extending through the barrel, with a plunger head or stopper disposed at the end of the plunger rod within the syringe barrel, and with a finger flange at the other end of the plunger rod extending out of the syringe barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the syringe barrel for attachment with a fluid line of a patient. Upon the user applying a force to depress the plunger rod and stopper through the syringe barrel towards the front end of the syringe barrel, the contents of the syringe are thereby forced out of the syringe barrel through the opening at the front end for delivery to the patient. Such an operation is well known in the medical field, and medical practitioners have become well accustomed to the use of such common fluid delivery procedures through standard syringes.

Conventional syringes are well known in the medical field to be used in connection with a vial of a medication, where the user collects or draws the fluid into the syringe immediately prior to injection and delivery of the fluid to the patient. Commonly, hypodermic syringes may be packaged as "pre-filled" devices, wherein the syringe is pre-filled with medication prior to being packaged and delivered to the patient. In this manner, the need for the user to fill the device prior to injection is eliminated, thereby saving time and maintaining consistent volumes for delivery.

However, packaging of such pre-filled syringes tends to be bulky and difficult to ship and store. A pre-filled syringe is typically packaged with the opening at the front end of the barrel including a cap thereover and with the plunger rod retracted out of the back end of the syringe barrel, with the fluid pre-filled within the syringe barrel. As conventional plunger rods are rigid and have a linear longitudinal axis, such packaging creates an elongated package that can be awkward for shipping and storage.

Pre-filled syringes and pre-filled metered dose syringes are often filled with fluids, such as a medication, at a production facility, packaged, and then shipped to the medical facility. Once at the facility, these syringes are often placed in controlled storage and/or locked cabinets to reduce theft of the syringes themselves and/or of the contents of these syringes. The space within these controlled storage locations is often limited, thus there is a need for a syringe assembly that has a uniform length in both a first filled position and a second dispensed position to reduce the amount of storage space required for containing the syringe both before use in a storage space and after use in a disposal container, and to allow for stacking of syringes within a storage cabinet and a disposal container.

SUMMARY OF THE INVENTION

In accordance with an embodiment of the present invention, a syringe assembly is provided which, in one embodiment, includes a plunger rod having a first end, a second end, and a rod portion extending therebetween, wherein at least a portion of the rod portion is flexible. The flexible portion of the plunger rod allows a stopper to be moved between a first position and a second position within a syringe barrel while the overall length of the syringe assembly remains the same throughout the movement between the first position and the second position. In this manner, the syringe assembly of the present disclosure allows a user to expel a fluid from the syringe and/or collect a fluid into the syringe while maintaining the same overall length of the syringe assembly. Advantageously, the space that the syringe assembly requires to be stored is the same in both a filled state and a dispensed state. Additionally, because syringe assemblies of the present disclosure have a uniform overall length in both a filled position and a dispensed position, the syringe assemblies can be stacked within a storage cabinet and a disposal container, thereby reducing the amount of space that the syringe assemblies occupy. In another embodiment, the present disclosure provides a syringe assembly including a restraining member adapted to communicate with the flexible portion of the plunger rod such that movement of a first end of the plunger rod in a first direction actuates movement of a second end of the plunger rod in a second direction different than the first direction.

The present disclosure, in one embodiment thereof, includes a syringe assembly including a syringe barrel having a first end, a second end, and a sidewall extending therebetween and defining a chamber having an interior. The syringe assembly of this embodiment includes a plunger rod having a first end, a second end, and a rod portion extending therebetween, wherein at least a portion of the rod portion is flexible. The syringe assembly further includes a stopper engaged with the second end of the plunger rod and slidably disposed within the interior of the chamber of the syringe barrel, the stopper sized relative to the interior of the chamber of the syringe barrel to provide sealing engagement with the sidewall of the syringe barrel. The syringe assembly further includes a restraining member adapted to communicate with the flexible portion of the plunger rod such that movement of the first end of the plunger rod in a first direction actuates movement of the second end of the plunger rod in a second direction, the second direction being different than the first direction.

In one configuration, the movement of the plunger rod in the second direction is substantially opposite the movement of the plunger rod in the first direction. In other configurations, a fluid may optionally be contained within the chamber. In still other configurations, an actuator flange may be disposed at least partially about the syringe barrel and connected to the first end of the plunger rod such that movement of the actuator flange in the first direction advances the first end of the plunger rod in the first direction and the second end of the plunger rod in the second direction. The actuator flange may include a projection, and the plunger rod may include a slot defined therein adjacent the first end of the plunger rod, the slot sized to accept the projection of the actuator flange therein.

The sidewall of the syringe barrel may include an outer surface, and the actuator flange comprises an inner surface, the actuator flange connected to the plunger rod such that a portion of the plunger rod is slidably restrained between the inner surface of the actuator flange and the outer surface of the syringe barrel. The actuator flange may include a key, and the restraining member may define a keyway, the keyway sized to accept the key of the actuator flange therein, the keyway sized relative to the key to guide movement of the actuator flange. In one configuration, the stopper includes a first engagement portion and the second end of the plunger rod comprises a second engagement portion for securely engaging the first engagement portion. The stopper may include a first threaded portion and the plunger rod may include a second threaded portion adjacent the second end of the plunger rod, the second threaded portion of the plunger rod threadingly engageable with the first threaded portion of the stopper to secure the plunger rod to the stopper.

A restraining member may include a top guide wall and a bottom guide wall, wherein the top guide wall and the bottom guide wall cooperate to form a guide channel, the guide channel sized to receive a portion of the plunger rod therein. In further configurations, movement of the second end of the plunger rod in the second direction actuates the stopper toward the first end of the syringe barrel. In still further configurations, a medication or a drug is disposed within the chamber of the syringe barrel.

The syringe assembly may be fully encapsulated by a packaging element. Alternatively, at least a portion of the syringe assembly may be encapsulated by a packaging element. In certain configurations, the packaging element includes a tear strip.

The present disclosure, in another embodiment thereof, includes a syringe assembly including a syringe barrel having a first end, a second end, and a sidewall extending therebetween and defining a chamber having an interior. The syringe assembly of this embodiment includes a stopper slidably disposed within the interior of the syringe barrel, the stopper sized relative to the interior of the chamber of the syringe barrel to provide sealing engagement with the sidewall of the syringe barrel. The syringe assembly further includes a plunger rod having a first end, a second end, and a rod portion extending therebetween, wherein at least a portion of the rod portion is flexible, wherein the second end of the plunger rod is engaged with the stopper such that movement of the first end of the plunger rod moves the stopper between a first position, in which the stopper is located a first distance from the first end of the syringe barrel, and a second position, in which the stopper is located a second distance from the first end of the syringe barrel, the second distance being different than the first distance, and wherein the plunger rod has a first effective distance in the first position relative to the syringe assembly and a second effective distance in the second position relative to the syringe assembly, the first effective distance and the second effective distance being equal.

In one aspect of the invention, the overall length of the syringe assembly is the same when the stopper is in the first position and the second position. In certain configurations, a fluid may be contained in the chamber. Optionally, the syringe assembly may include an actuator flange disposed at least partially about the syringe barrel and connected to the first end of the plunger rod such that movement of the actuator flange in a first direction advances the first end of the plunger rod in the first direction and the second end of the plunger rod in a second direction. The actuator flange may include a projection, and the plunger rod may include a slot defined therein adjacent the first end of the plunger rod, the slot sized to accept the projection of the actuator flange therein.

The sidewall of the syringe barrel may include an outer surface, and the actuator flange may include an inner surface, the actuator flange connected to the plunger rod such that a portion of the plunger rod is slidably restrained between the inner surface of the actuator flange and the outer surface of the syringe barrel. The stopper may also include a first engagement portion and the second end of the plunger rod may include a second engagement portion for securely engaging the first engagement portion. In certain configurations, the stopper includes a first threaded portion, and the plunger rod includes a second threaded portion adjacent the second end of the plunger rod, the second threaded portion of the plunger rod threadingly engageable with the first threaded portion of the stopper to secure the plunger rod to the stopper.

The syringe assembly may be fully encapsulated by a packaging element. Alternatively, at least a portion of the syringe assembly may be encapsulated by a packaging element. In certain configurations, the packaging element includes a tear strip.

The present disclosure, in a further embodiment thereof, includes a syringe assembly including a syringe barrel having a first end, a second end, and a sidewall extending therebetween and defining a chamber having an interior. The syringe assembly of this embodiment includes a stopper slidably disposed within the interior of the chamber of the syringe barrel, the stopper sized relative to the interior of the chamber of the syringe barrel to provide sealing engagement with the sidewall of the syringe barrel. The syringe assembly further includes a plunger rod having a first end, a second end, and a rod portion extending therebetween, wherein at least a portion of the rod portion is flexible, wherein the second end of the plunger rod is engaged with the stopper such that movement of the first end of the plunger rod moves the stopper between a first position, in which the stopper is located a first distance from the first end of the syringe barrel, and a second position, in which the stopper is located a second distance from the first end of the syringe barrel, the second distance being different than the first distance, and wherein the overall length of the syringe assembly is the same when the stopper is in the first position and the second position.

In certain configurations, the plunger rod has a first effective distance in the first position relative to the syringe assembly, and a second effective distance in the second position relative to the syringe assembly, the first effective distance and the second effective distance being equal. In other configurations, a fluid may be contained in the chamber. In further configurations, the stopper may include a first engagement portion and the second end of the plunger rod may include a second engagement portion for securely engaging the first engagement portion. In still further configurations, the stopper may include a first threaded portion, and the plunger rod may include a second threaded portion adjacent the second end of the plunger rod, the second threaded portion of the plunger rod threadingly engageable with the first threaded portion of the stopper to secure the plunger rod to the stopper.

The syringe assembly may be fully encapsulated by a packaging element. Alternatively, at least a portion of the syringe assembly may be encapsulated by a packaging element. In certain configurations, the packaging element includes a tear strip.

BRIEF DESCRIPTION OF THE DRAWINGS

FIG. 1 is an exploded, perspective view of a syringe assembly in accordance with an embodiment of the present invention.

FIG. 2D is a perspective view of the syringe assembly of FIG. 2A with a cap removed from the syringe assembly in accordance with an embodiment of the present invention.

FIG. 4B is a cross-sectional view of the syringe assembly taken along line 4B-4B of FIG. 4A in accordance with an embodiment of the present invention.

FIG. 4C is a cross-sectional view of the syringe assembly taken along line 4C-4C of FIG. 4B in accordance with an embodiment of the present invention.

FIG. 8B is a side perspective view of the syringe assembly of FIG. 8A in accordance with an embodiment of the present invention.

DETAILED DESCRIPTION

Figure 2A:
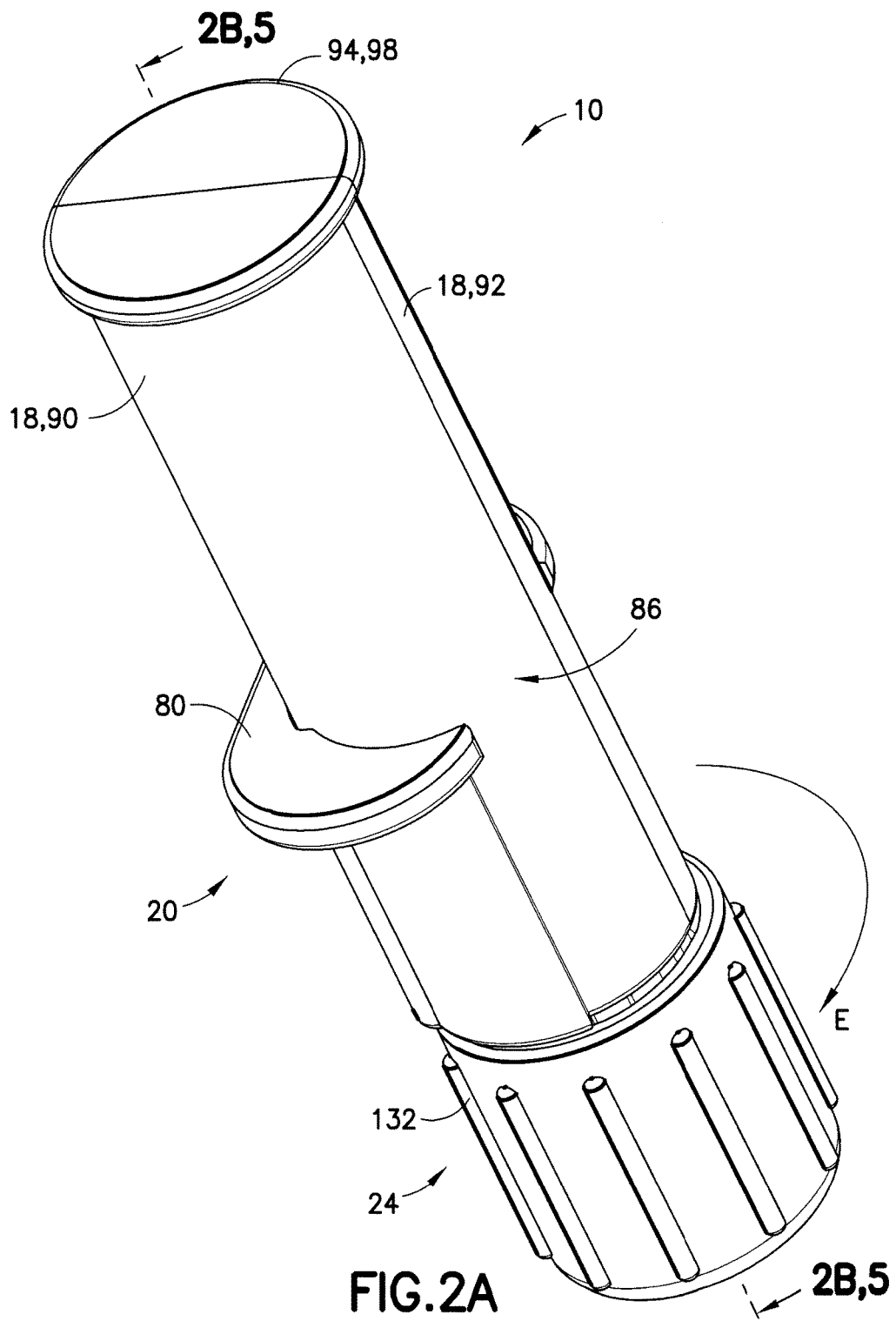
FIG. 2A is an assembled, perspective view of the syringe assembly of FIG. 1 in a first position in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe assembly adapted for engagement with a separate device such as a needle assembly or IV connection assembly, and "proximal" refers to the opposite direction of distal, i.e., away from the end of a syringe assembly adapted for engagement with the separate device. For purposes of this disclosure, the above-mentioned references are used in the description of the components of a syringe assembly in accordance with the present disclosure.

Referring to FIG. 1, a syringe assembly 10 includes a syringe barrel 12, a plunger rod 14, a stopper 16, a restraining member or guide member 18, an actuator flange 20, a fitting 22, a cap 24, and a seal 26. Syringe assembly 10 may be adapted for the dispensing and delivery of a fluid and/or collection of a fluid. For example, syringe assembly 10 may be used for injection or infusion of fluid such as a medication into a patient. Syringe assembly 10 is contemplated for use in connection with a needle, such as by connecting syringe assembly 10 to a separate needle assembly (not shown), or alternatively for connection with an intravenous (IV) connection assembly (not shown). It can be appreciated that the present disclosure can be used with any type of syringe assembly, particularly those which are placed in a controlled storage environment in which storage space is limited. These types of syringes include traditional pre-filled syringe assemblies, metered dose syringes, aspiration syringes for withdrawing fluid from a patient or medication from a container, and the like.

Figure 2B:
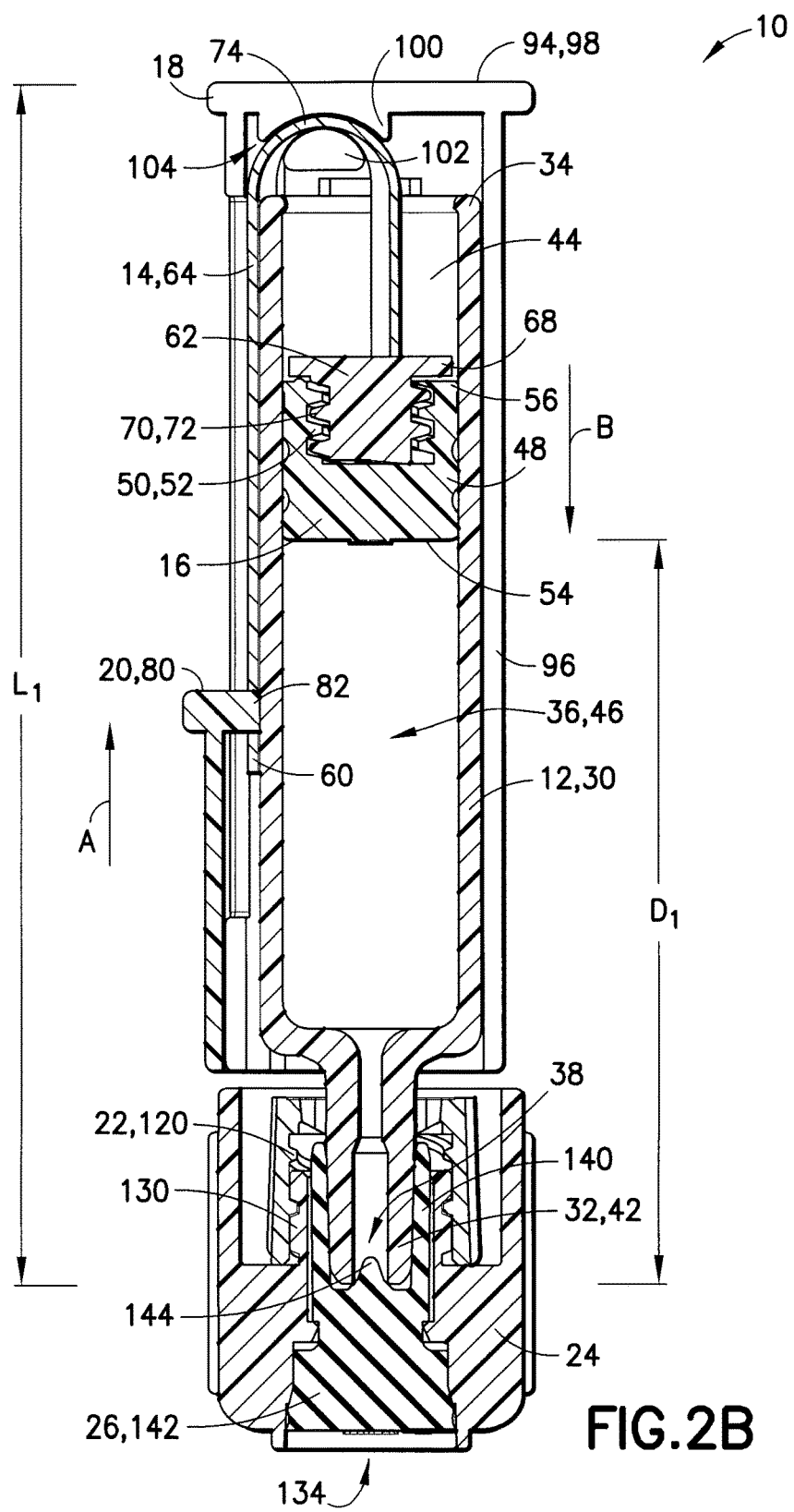
FIG. 2B is a cross-sectional view taken along line 2B-2B of FIG. 2A in accordance with an embodiment of the present invention.

Referring to FIGS. 1, 2B, and 4B, syringe barrel 12 generally includes a barrel body or sidewall 30 extending between a first or distal end 32 and a second or proximal end 34. Sidewall 30 defines an elongate aperture or interior chamber 36 of syringe barrel 12. In one embodiment, interior chamber 36 may span the extent of syringe barrel 12 so that syringe barrel 12 is cannulated along its entire length. In one embodiment, syringe barrel 12 may be in the general form of an elongated cylindrical barrel as is known in the art in the general shape of a hypodermic syringe. In alternative embodiments, syringe barrel 12 may be in other forms for containing a fluid for delivery, such as in the general form of an elongated rectangular barrel, for example. Syringe barrel 12 may be formed of glass, or may be injection molded from thermoplastic material such as polypropylene and polyethylene according to techniques known to those of ordinary skill in the art, though it is to be appreciated that syringe barrel 12 may be made from other suitable materials and according to other applicable techniques.

Referring to FIG. 1, distal end 32 of syringe barrel 12 includes an outlet opening 38 which is in fluid communication with chamber 36. Outlet opening 38 may be sized and adapted for engagement with a separate device, such as a needle assembly or IV connection assembly and, therefore, may include a mechanism for such engagement as is conventionally known. For example, distal end 32 may include a generally-tapered luer tip 42 for engagement with an optional separate tapered luer mating surface of such a separate device for attachment therewith (not shown). In addition, a mechanism for locking engagement therebetween may also be provided, such as luer fitting 22 including interior threaded portion 120 (FIG. 2B). Such luer connections and luer locking mechanisms are well known in the art.

Proximal end 34 of syringe barrel 12 is generally open-ended, but is intended to be closed off to the external environment as will be discussed herein. Syringe barrel 12 may also include fill lines 40 (FIG. 8B), such as graduations located on sidewall 30, for providing an indication as to the level or amount of fluid contained within interior chamber 36 of syringe barrel 12. Such markings may be provided on an external surface of sidewall 30, an internal surface of sidewall 30, or integrally formed or otherwise within sidewall 30 of syringe barrel 12. In other embodiments, alternatively, or in addition thereto, the markings may also provide a description of the contents of the syringe or other identifying information such as maximum and/or minimum fill lines.

Referring to FIGS. 1, 2B, and 4B, syringe assembly 10 includes stopper 16 which is slidably disposed within interior chamber 36, and in sealing contact with the internal surface of sidewall 30 of syringe barrel 12, thereby separating interior chamber 36 into a proximal chamber 44 (FIGS. 2B and 4B) adjacent proximal end 34, and a distal chamber 46 (shown specifically in FIG. 2B) adjacent distal end 32. Stopper 16 is sized relative to syringe barrel 12 to provide sealing engagement with the interior surface of sidewall 30 of syringe barrel 12. Additionally, stopper 16 may include one or more annular ribs 48 extending around the periphery of stopper 16 to increase the sealing engagement between stopper 16 and the interior surface of sidewall 30 of syringe barrel 12. In alternate embodiments, a singular O-ring or a plurality of O-rings may be circumferentially disposed about stopper 16 to increase the sealing engagement with the interior surface of sidewall 30. Referring to FIGS. 1, 2B, and 4B, stopper 16 also includes distal end 54 and proximal end 56 defining a plunger receiving aperture 50 having an engagement portion for securing plunger rod 14 to stopper 16. In one embodiment, the engagement portion of stopper 16 may include an interior threaded portion 52 for engagement with plunger rod 14 as will be described below. In other embodiments, the engagement portion of stopper 16 may include a snap fit mechanism, a ball detent, locking tabs, spring loaded locking mechanism, latch, adhesive, or other similar mechanism. In another embodiment, plunger rod 14 and stopper 16 may be co-formed such as by co-extrusion.

Referring to FIGS. 1, 2B, and 4B, syringe assembly 10 further includes plunger rod 14 which provides a mechanism for dispensing fluid contained within interior chamber 36 of syringe barrel 12 through outlet opening 38. Plunger rod 14 is adapted for advancing stopper 16 within barrel 12. At least a portion of plunger rod 14 is flexible. In one embodiment, plunger rod 14 is sized for movement within interior chamber 36 of syringe barrel 12 and outside of syringe barrel 12, as will be discussed in more detail below. Plunger rod 14 generally includes an actuator flange engaging end or first end 60, an opposing stopper engaging end or second end 62, a rod portion 64 extending between first end 60 and second end 62, a slot 66 disposed adjacent first end 60, a flange 68 disposed adjacent second end 62, and an engagement portion for securing plunger rod 14 to stopper 16. In one embodiment, the engagement portion of plunger rod 14 may include a stopper engagement member 70 including a threaded portion 72 disposed adjacent second end 62. In other embodiments, the engagement portion of plunger rod 14 may include a snap fit mechanism, a ball detent, locking tabs, spring loaded locking mechanism, latch, adhesive, or other similar mechanism.

At least a portion of rod portion 64 is made of a flexible material. For example, referring to FIG. 2B, rod portion 64 includes a flexible portion 74. Flexible portion 74 of rod portion 64 may be formed of various elastomers including silicone or rubberized materials. In other configurations, the flexible portion 74 may be formed of a flexible metal, such as a solid or linked flexible metal belt. In still other configurations, the flexible portion 74 may be a metal ball-and-pin chain. In one configuration, the materials used to make flexible portion 74 of plunger rod 14 may have a generally low modulus of elasticity and a high yield strain as compared with other materials. In one embodiment, the entirety of rod portion 64 may be formed of a flexible material. In other embodiments, rod portion 64 may be formed of separate materials and/or elements that are attached or otherwise interconnected together. For example, a first portion of rod portion 64 may be constructed of a rigid polymeric material and a second portion of rod portion 64 may be constructed of a flexible material such as an elastomer. In such an embodiment, the rigid portion of rod portion 64 and the flexible portion of rod portion 64 may be mechanically attached together or adhesively fixed together, or molded integrally such as through a two-shot molding process. In alternative embodiments, rod portion 64 may include hinged portions.

Because at least a portion of rod portion 64 is made of a flexible material, in one embodiment, actuation of first end 60 of plunger rod 14 in a direction generally along arrow A (FIG. 2B) actuates movement of second end 62 of plunger rod 14 in a direction generally along arrow B (FIG. 2B) via flexible portion 74, as will be discussed in more detail below. Additionally, in one embodiment, flexible portion 74 of plunger rod 14 allows actuation of first end 60 of plunger rod 14 in a direction generally along arrow C (FIG. 5) to actuate movement of second end 62 of plunger rod 14 in a direction generally along arrow D (FIG. 5) via flexible portion 74, as will be discussed in more detail below.

In one embodiment, referring to FIGS. 2B and 4B, plunger rod 14 may be secured to stopper 16 by positioning stopper 16 into engagement with a portion of plunger rod 14. In one embodiment, plunger rod 14 may be secured to stopper 16 by positioning stopper engagement portion 70 of plunger rod 14 into engagement with plunger receiving aperture 50 of stopper 16, and threadingly engaging threaded portion 72 of plunger rod 14 to interior threaded portion 52 of stopper 16. In other embodiments, plunger rod 14 can be secured to stopper 16 using a press-fit, ball detent, locking tabs, spring loaded locking mechanism, latch, adhesive, or other similar mechanism, as discussed above. In another embodiment, plunger rod 14 and stopper 16 may be co-formed such as by co-extrusion. In this manner, plunger rod 14 is locked to stopper 16, i.e., significant relative movement between plunger rod 14 and stopper 16 is prevented and movement of plunger rod 14 can be transferred to stopper 16 to slide stopper 16 between positions within syringe barrel 12. In alternate embodiments, plunger rod 14 and stopper 16 may be integrally formed as a plunger assembly.

Figure 4A:
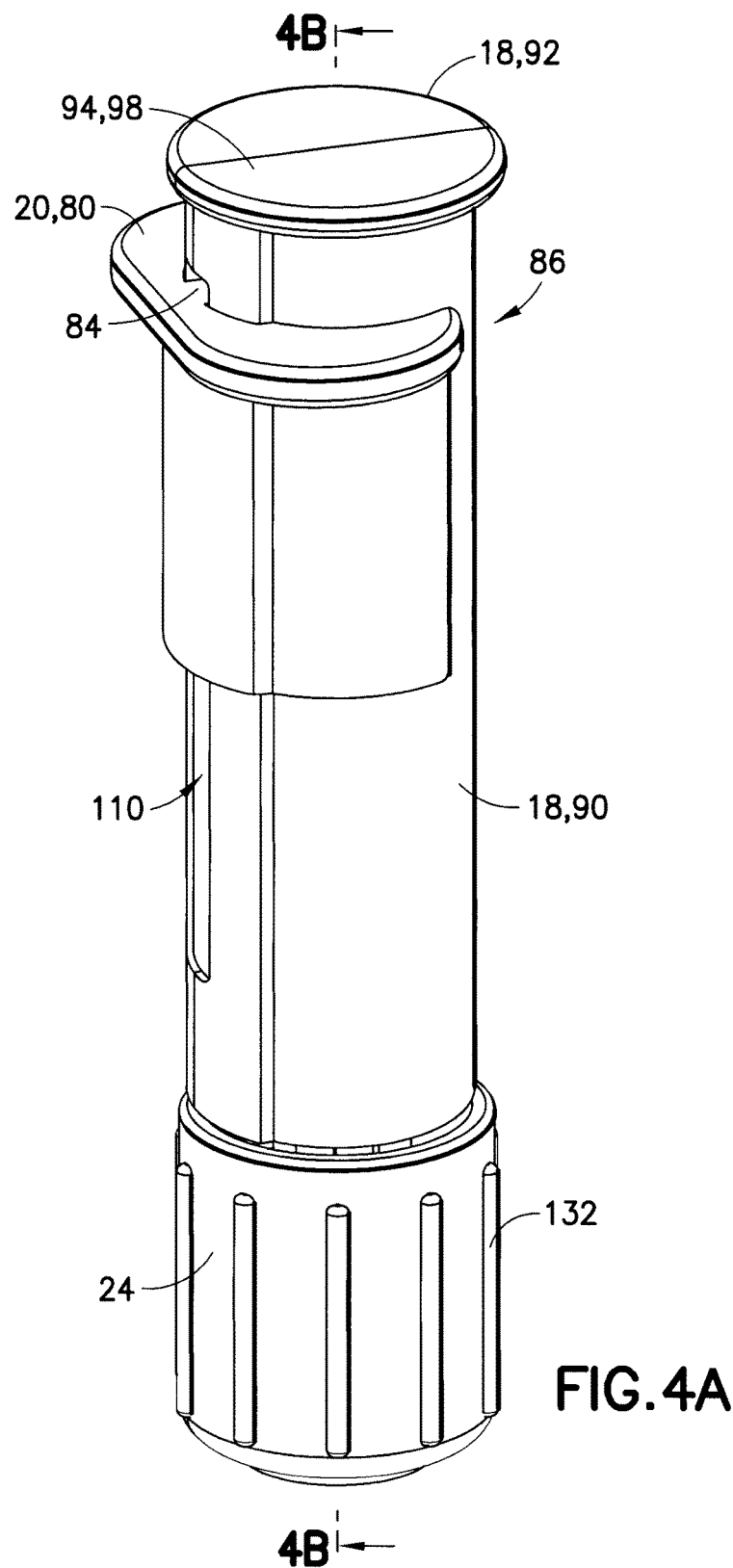
FIG. 4A is a perspective view of the syringe assembly of FIG. 1 in a second position in accordance with an embodiment of the present invention.

Initial movement of first end 60 of plunger rod 14 may be effected by a portion of plunger rod 14 or by a separate actuation means which at least partially extends externally outside of syringe barrel 12. For example, actuator flange or C-shaped flange 20 (FIGS. 1, 2B, and 4B), together with plunger rod 14, may provide actuation means for moving stopper 16 between a first position (FIGS. 2A and 2B) and a second position (FIGS. 4A and 4B). In the first position, stopper 16 is located a first distance $D_1$ from distal end 32 of syringe barrel 12, as shown in FIG. 2B, and in the second position, stopper 16 is located a second distance $D_2$ from distal end 32 of syringe barrel 12 as shown in FIG. 4B, second distance $D_2$ being different than first distance $D_1$. In one embodiment, an actuator in the form of C-shaped flange 20 may extend external to syringe barrel 12, for example, along the external surface of restraining member 18, restraining member 18 being located over syringe barrel 12, as will be discussed in more detail below. FIGS. 1-5 illustrate actuator flange 20 having a C-shape, though it is contemplated that other shapes of flange 20 may be used. For example, actuator flange 20 may have any shape that allows a user to grip and actuate flange 20 in a back and forth direction.

Figure 2C:
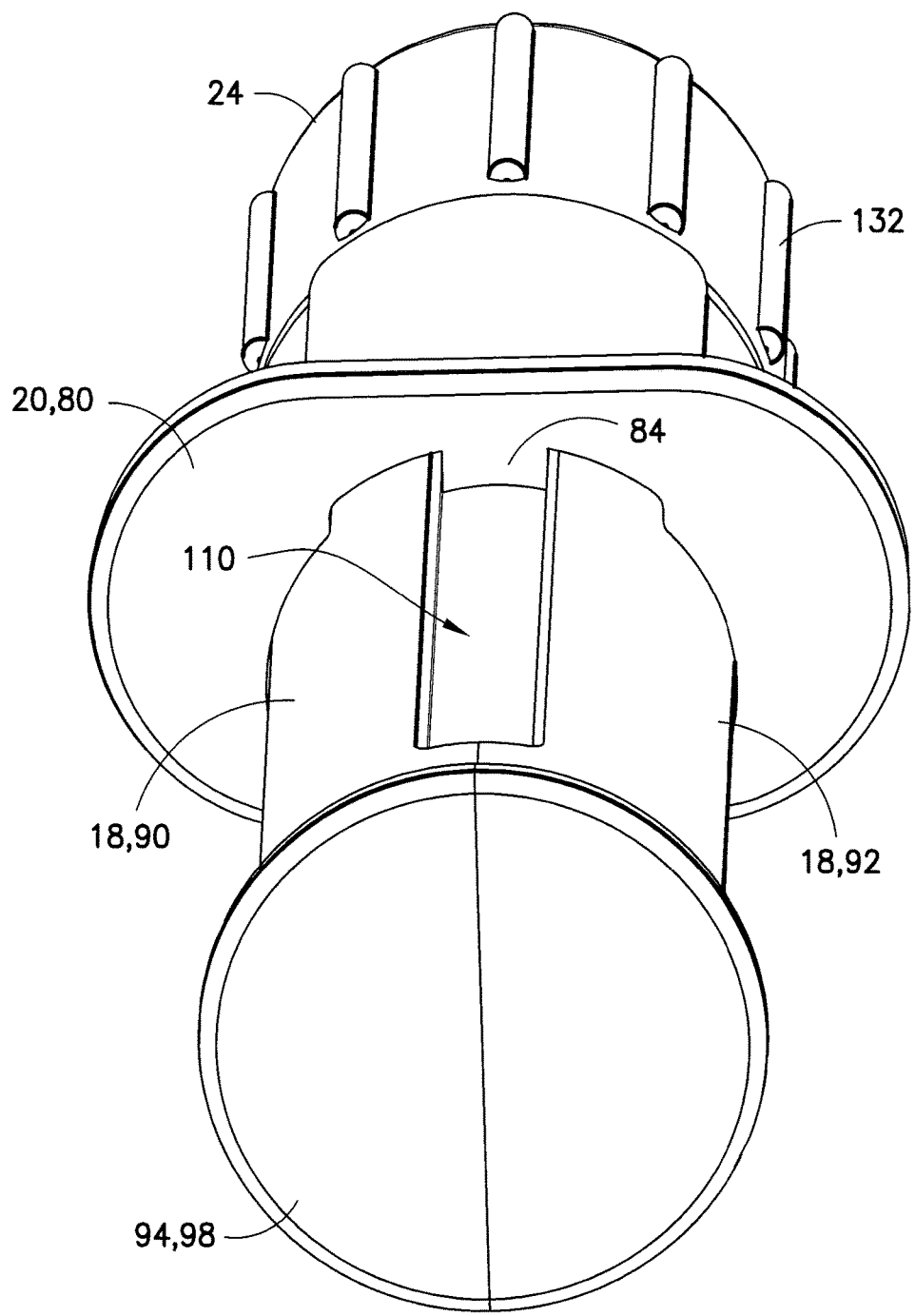
FIG. 2C is a perspective view of the syringe assembly of FIG. 2A in the first position, with a keyed portion of a C-shaped flange engaged with a keyway of an outer housing portion of the syringe assembly in accordance with an embodiment of the present invention.
Figure 3A:
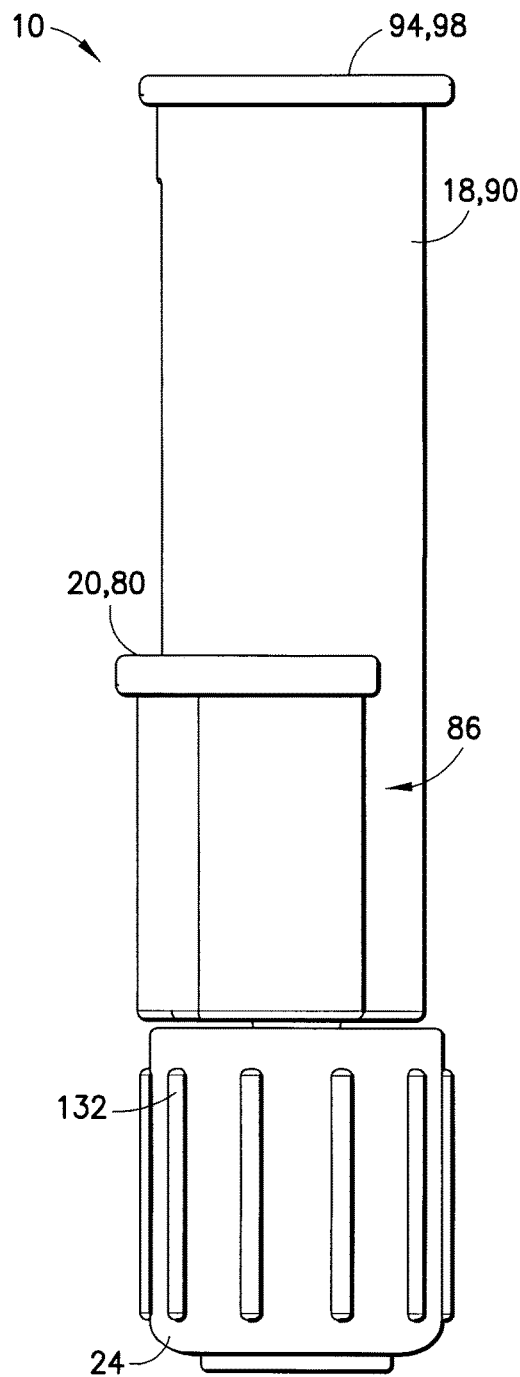
FIG. 3A is a side elevation view of the syringe assembly of FIG. 2A in accordance with an embodiment of the present invention.
Figure 3B:
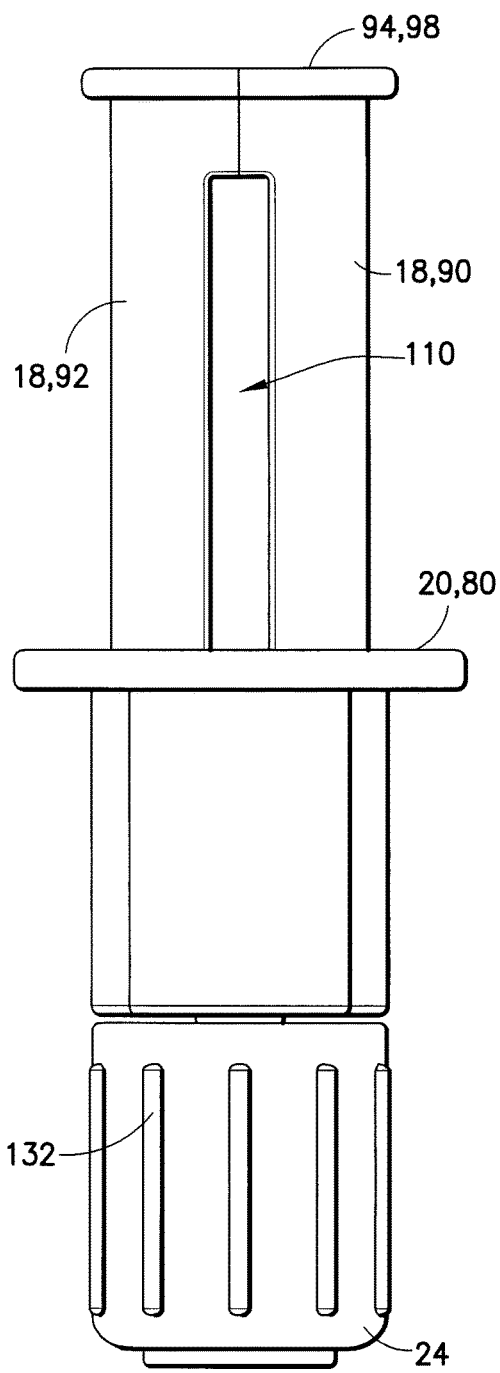
FIG. 3B is a second side elevation view of the syringe assembly of FIG. 3A rotated 90 degrees in a counterclockwise direction in accordance with an embodiment of the present invention.
Figure 3C:
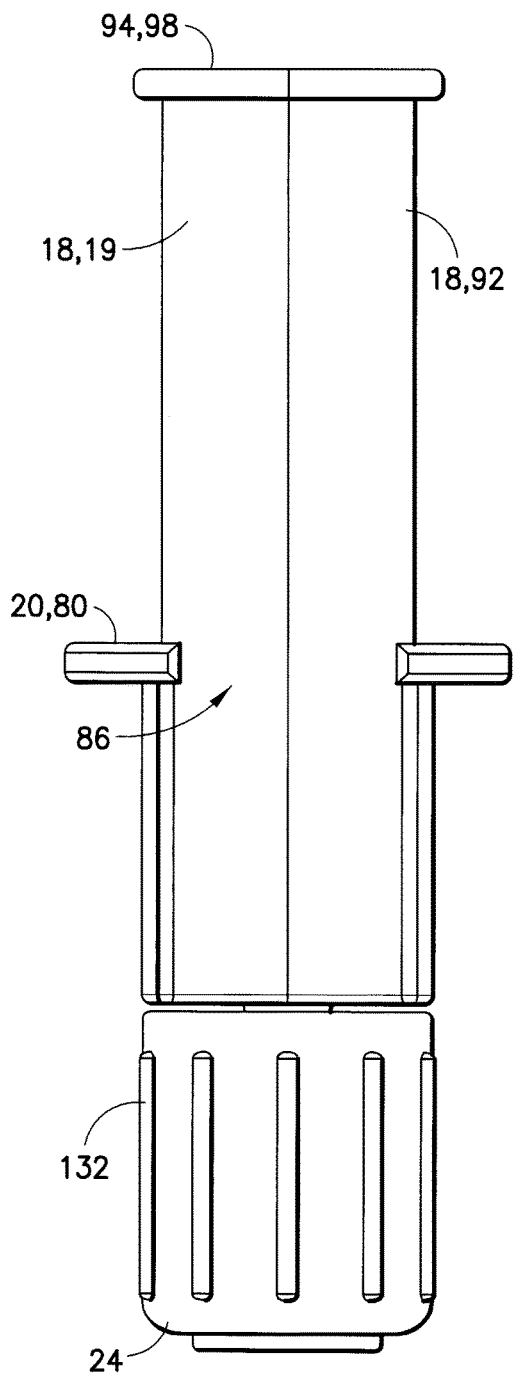
FIG. 3C is a third side elevation view of the syringe assembly of FIG. 3A rotated 90 degrees in a clockwise direction in accordance with an embodiment of the present invention.
Figure 3D:
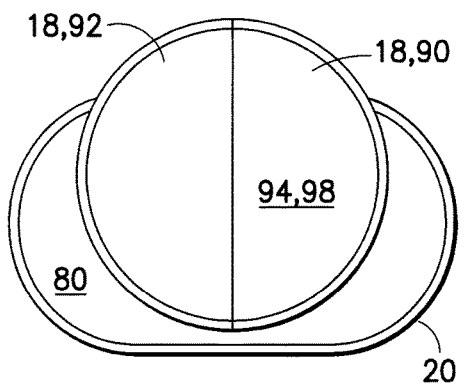
FIG. 3D is a plan view of the syringe assembly of FIG. 3A in accordance with an embodiment of the present invention.
Figure 3E:
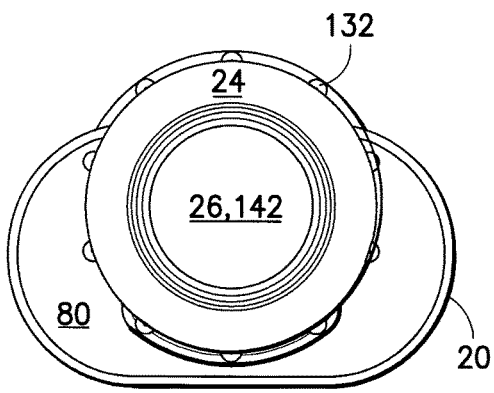
FIG. 3E is a bottom view of the syringe assembly of FIG. 3A in accordance with an embodiment of the present invention.

Referring to FIGS. 1, 2B, 2C, and 4B, C-shaped flange 20 generally includes a finger flange 80, a locking projection 82 (FIG. 2B), and a keyed portion 84 (FIG. 2C). In one embodiment, flange 20 has a generally C-shape with an open side 86 (FIG. 1), although it is contemplated that other configurations of flange 20 may be used in accordance with the present disclosure to actuate plunger rod 14. Open side 86 allows visibility for a user to see fill lines 40 (FIGS. 8B and 10A) on syringe barrel 12. Referring to FIGS. 2B and 4B, C-shaped flange 20 may be interconnected with plunger rod 14 via engagement of locking projection 82 of flange 20 in slot 66 of plunger rod 14. In alternative embodiments, flange 20 may be secured to plunger rod 14 using a ball detent, spring-loaded locking mechanisms, latches, or other similar mechanisms. In this manner, movement of flange 20 advances plunger rod 14 and movement of plunger rod 14 can be transferred to stopper 16 to slide stopper 16 between positions within syringe barrel 12. The connection between flange 20 and plunger rod 14 also provides a mechanism for slidably restraining a portion of plunger rod 14 between an inner surface of flange 20 and an outer surface of syringe barrel 12.

Referring to FIG. 1, restraining member 18 generally includes a corresponding first half 90 and a second half 92 that may be mirror images of each other or may have different shapes. Referring to FIGS. 2B and 4B, first half 90 and second half 92 are configured to mate and cooperatively form a cap end 94, a side wall 96, a finger pad portion 98, an arcuate guide wall or top guide wall 100, and an opposing bottom guide wall 102. Together top guide wall 100 and bottom guide wall 102 cooperate to form a guide channel 104 which receives flexible portion 74 of plunger rod 14 and guides plunger rod 14 upon actuation of plunger rod 14 via actuator flange 20. Restraining member 18 is secured to syringe barrel 12 as shown in FIGS. 2B, 4B, and 4C. In one embodiment, first half 90 and second half 92 of restraining member 18 can be secured to syringe barrel 12 via a snap-fit system including locking features on one of first half 90 and second half 92 and mating features on the other of first half 90 and second half 92. In other embodiments, latching systems, fasteners, or similar securement mechanisms can be used to secure restraining member 18 to syringe barrel 12. In alternate embodiments, restraining member 18 could be molded in more than two halves, or could be molded in a singular cylindrical-shaped restraining member 18.

Referring to FIG. 4C, restraining member 18 includes a first arm 106 and a second arm 108 together forming an opening or keyway 110. Referring to FIG. 2C, keyed portion 84 of actuator flange 20 is received within keyway 110 of restraining member 18. In this manner, keyed portion 84 and keyway 110 provide proper alignment of actuator flange 20 relative to restraining member 18 and syringe barrel 12, guiding movement of actuator flange 20 in a direction generally along arrow A (FIG. 2B) and in a direction generally along arrow C (FIG. 5), and first arm 106 and second arm 108 provide a physical barrier to resist rotation of actuator flange 20 around syringe barrel 12.

Also, referring to FIG. 4C, first arm 106 and second arm 108 provide a guide channel to plunger rod 14 such that plunger rod 14 is disposed between first arm 106 and second arm 108 of restraining member 18 and the outer surface of syringe barrel 12. In this manner, first arm 106 and second arm 108 guide movement of plunger rod 14 relative to syringe barrel 12 and prevent lift-off of plunger rod 14 from the outer surface of syringe barrel 12, i.e., during movement of first end 60 of plunger rod 14 in a direction generally along arrow A (FIG. 2B) or in a direction generally along arrow C (FIG. 5); and first arm 106 and second arm 108 prevent plunger rod 14 from movement in a direction generally perpendicular to the direction generally along arrow A (FIG. 2B) away from the outer surface of syringe barrel 12.

Referring to FIGS. 2B and 4B, top guide wall 100 and bottom guide wall 102 cooperate to define guide channel 104. Flexible portion 74 of plunger rod 14 is received in guide channel 104 and top guide wall 100 and bottom guide wall 102 guide plunger rod 14 such that movement of first end 60 of plunger rod 14 in a first direction actuates movement of second end 62 of plunger rod 14 in a second direction, the second direction being different than the first direction. For example, referring to FIG. 2B, upon movement of first end 60 of plunger rod 14 in a direction generally along arrow A, top guide wall 100 provides a physical barrier preventing plunger rod 14 from further movement in the direction generally along arrow A. At this point, top guide wall 100 provides a physical barrier deforming the shape of plunger rod 14, i.e., flexible portion 74. Movement of flexible portion 74 of plunger rod 14 is guided through guide channel 104 between the respective barriers of top guide wall 100 and bottom guide wall 102. In this manner, movement of first end 60 of plunger rod 14 in a direction generally along arrow A actuates movement of second end 62 of plunger rod 14 in a direction generally along arrow B (FIG. 2B), i.e., movement of first end 60 of plunger rod 14 in a direction generally along arrow A is directed by top guide wall 100 and bottom guide wall 102 to move second end 62 of plunger rod 14 in a direction generally along arrow B via flexible portion 74.

Referring to FIG. 2B, fitting 22 includes an interior threaded portion 120 and is secured to distal end 32 of syringe barrel 12. Referring to FIG. 2B, cap 24 includes a threaded portion 130, with ribs 132 (shown in FIG. 1) disposed on an exterior surface of cap 24, and a seal aperture 134 extending through the extent of cap 24. Cap 24 is threadingly connected to fitting 22 via mating threaded portions 120, 130 as shown in FIG. 2B. Ribs 132 of cap 24 provide a gripping means to allow a user or a tool to more easily grasp cap 24 when threading cap 24 to fitting 22 or removing cap 24 from fitting 22. Referring to FIGS. 1 and 2B, seal member 26 includes a seal body 140, a seal head 142, and a seal protrusion 144. Seal member 26 can be positioned through seal aperture 134 of cap 24 and secured over distal end 32 of syringe barrel 12 with seal body 140 between interior threaded portion 120 of fitting 22 and distal end 32 of syringe barrel 12. In this manner, a seal protrusion 144 extends into outlet opening 38 of syringe barrel 12 to seal any liquid contained in distal chamber 46 of syringe barrel 12 from leaking out. In this position, a seal head 142 also fills and seals seal aperture 134 of cap 24.

Syringe assembly 10 may be useful as a pre-filled syringe, and, therefore, may be provided for end use with a fluid, such as a medication, contained within distal chamber 46 of syringe barrel 12, pre-filled by the manufacturer. In this manner, syringe assembly 10 can be manufactured, pre-filled with a medication, sterilized, and packaged in appropriate packaging for delivery, storage, and use by the end user, without the need for the end user to fill the syringe with medication from a separate vial prior to use. In such an embodiment, syringe assembly 10 may include cap 24 and seal member 26 disposed at distal end 32 of syringe barrel 12 to seal a fluid, such as a medication, within distal chamber 46 of syringe barrel 12 as described above. All of the components of syringe assembly 10 may be constructed of any known material, and are desirably constructed of medical-grade polymers.

Figure 10B:
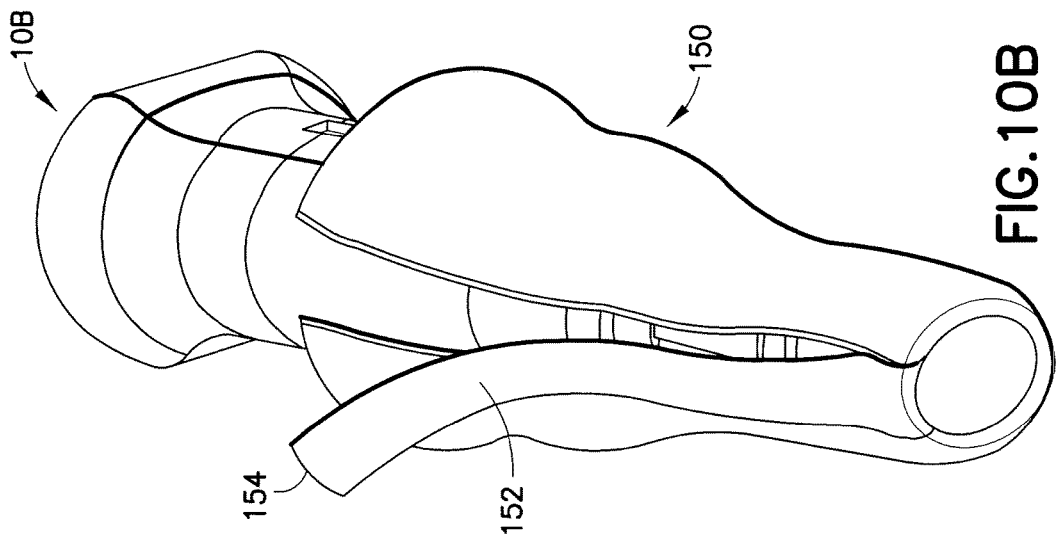
FIG. 10B is a perspective view of the syringe assembly of FIG. 10A with a tear strip opened to indicate evidence of tampering in accordance with an embodiment of the present invention.
Figure 10A:
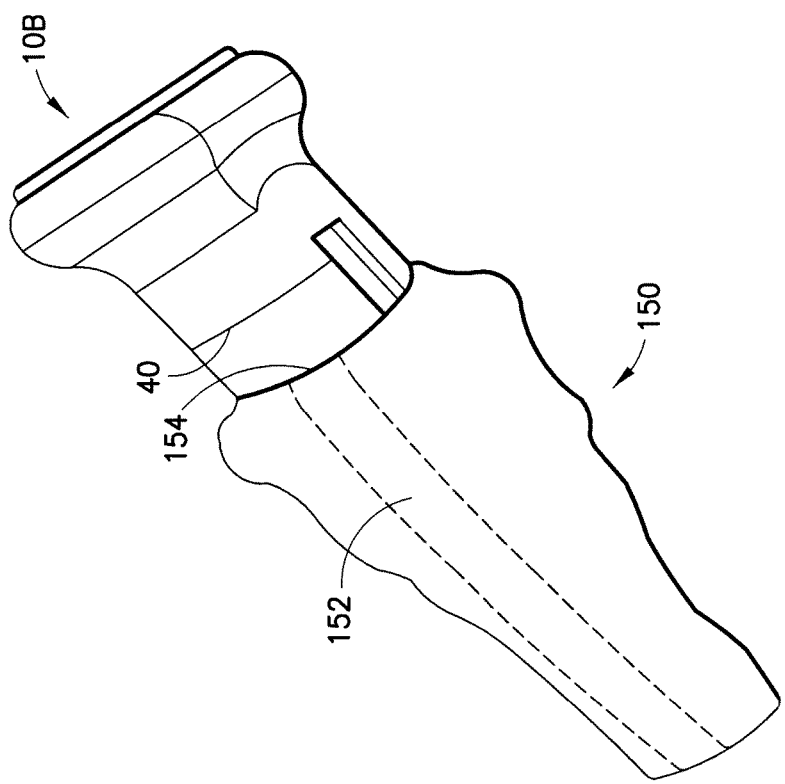
FIG. 10A is a perspective view of a syringe assembly including packaging thereon in accordance with an embodiment of the present invention.

Referring to FIGS. 1-4B, the use of syringe assembly 10 to expel a fluid, such as a medication, contained within distal chamber 46 of syringe barrel 12 will now be described. Initially, the user removes syringe assembly 10 from any protective packaging. Referring to FIG. 10A, syringe assembly 10 may be fully or partially encapsulated in a packaging 150 which provides protection to syringe assembly 10 and any pre-filled medication therein. Packaging 150 includes a tear strip 152. Before use, referring to FIGS. 10A and 10B, a user can grasp a proximal end 154 of tear strip 152 and pull tear strip 152 longitudinally to remove packaging 150 from syringe assembly 10. Tear strip 152 has a sufficient thickness to withstand potential impact forces applied to packaging 150 before use of syringe assembly 10, but is sufficiently thin to tear when pulled longitudinally. Proximal end 154 of tear strip 152 can be pulled by hand but also may be removed by tools. Next, referring to FIGS. 2A and 2D, a user removes seal member 26 from distal end 32 of syringe barrel 12, and cap 24 can be removed from fitting 22 by rotating cap 24 clockwise, i.e., in the direction of arrow E (FIG. 2A). A user can then attach tip 42 of syringe barrel 12 to a separate needle assembly or IV connection assembly and lockingly engage the needle assembly or IV connection assembly to tip 42 of syringe barrel 12 in a known manner. Prior to dispensing any medication, any air trapped within distal chamber 46 of syringe barrel 12 can be expelled in a known manner.

When it is desired to expel or deliver the medication contained within syringe barrel 12, syringe assembly 10 is grasped with the user's thumb on a finger pad portion 98 of restraining member 18 and with the user's fingers extending around finger flange 80 of actuator flange 20. In this manner, syringe assembly 10 is grasped by a user in a well known and well recognized manner similar to the operation of a conventional hypodermic syringe. Next, the user effects a squeezing movement between the thumb on finger pad portion 98 of restraining member 18 and four fingers grasping finger flange 80 of actuator flange 20, thereby causing actuator flange 20 to move in a direction generally along arrow A (FIG. 2B) toward proximal end 34 of syringe barrel 12. Referring to FIG. 2B, such movement of actuator flange 20 advances movement of first end 60 of plunger rod 14 in the direction generally along arrow A via engagement of locking projection 82 of flange 20 and slot 66 of plunger rod 14 as described above. Movement of first end 60 of plunger rod 14 in the first direction generally along arrow A actuates movement of second end 62 of plunger rod 14 in a second direction generally along arrow B different than the first direction. This is accomplished by flexible portion 74 of plunger rod 14 being received in guide channel 104, and top guide wall 100 and bottom guide wall 102 of restraining member 18 guiding plunger rod 14 as described in detail above. In this manner, movement of stopper 16 in the direction generally along arrow B forces the fluid contained within distal chamber 46 of syringe barrel 12 to be forced out of outlet opening 38. The fluid can be expelled from syringe barrel 12 through outlet opening 38 into a separate needle assembly or IV assembly and into the patient.

Referring to FIGS. 2B and 4B, actuator flange 20 and plunger rod 14 provide actuation means for moving stopper 16 between an initial or first position (FIGS. 2A and 2B) and a second position (FIGS. 4A and 4B). Referring to FIG. 2B, in the first position stopper 16 is located a first distance $D_1$ from distal end 32 of syringe barrel 12. Referring to FIG. 4B, in the second position stopper 16 is located a second distance $D_2$ from distal end 32 of syringe barrel 12. Movement of stopper 16 from the first position shown in FIG. 2B to the second position shown in FIG. 4B reduces the volume of distal chamber 46 and forces the fluid from syringe barrel 12.

By having plunger rod 14 including flexible portion 74, the length of syringe assembly 10 is the same with stopper 16 in the first position (FIG. 2B) and the second position (FIG. 4B), i.e., the length of syringe assembly 10 remains the same during movement of first end 60 of plunger rod 14 in the first direction generally along arrow A and movement of second end 62 of plunger rod 14 in the second direction generally along arrow B. For example, referring to FIGS. 2B and 4B, the overall length of syringe assembly 10 is equal to length $L_1$ with stopper 16 in the first position (FIG. 2B) and the overall length of syringe assembly 10 is equal to length $L_2$ with stopper 16 in the second position (FIG. 4B). Overall lengths $L_1$ and $L_2$ of syringe assembly 10, including the length of syringe barrel 12 and the length of plunger rod 14, extending outwardly from syringe barrel 12 in the proximal direction, are equal in the first position (FIG. 2B) and the second position (FIG. 4B) and all positions therebetween. In other words, plunger rod 14 has a first effective distance in the first position (FIG. 2B) relative to syringe assembly 10, and plunger rod 14 has a second effective distance in the second position (FIG. 4B) relative to syringe assembly 10, the first effective distance and the second effective distance of plunger rod 14 being equal in both positions, i.e., lengths $L_1$ and $L_2$ of syringe assembly 10 are equal in the first position (FIG. 2B) and the second position (FIG. 4B) and all positions therebetween.

In this manner, the length of syringe assembly 10 is the same in a filled position and in a dispensed position and a plunger rod in accordance with the present disclosure takes up the same amount of space in all positions. The length of syringe assembly 10 when filled with fluid prior to use is significantly reduced when compared with a traditional syringe. This reduced length allows syringe assembly 10 to occupy little space prior to use, thereby reducing packaging and eliminating waste. Further, syringe assembly 10 takes up the same amount of space in a dispensed state for disposal such as in a sharps disposal container.

Figure 5:
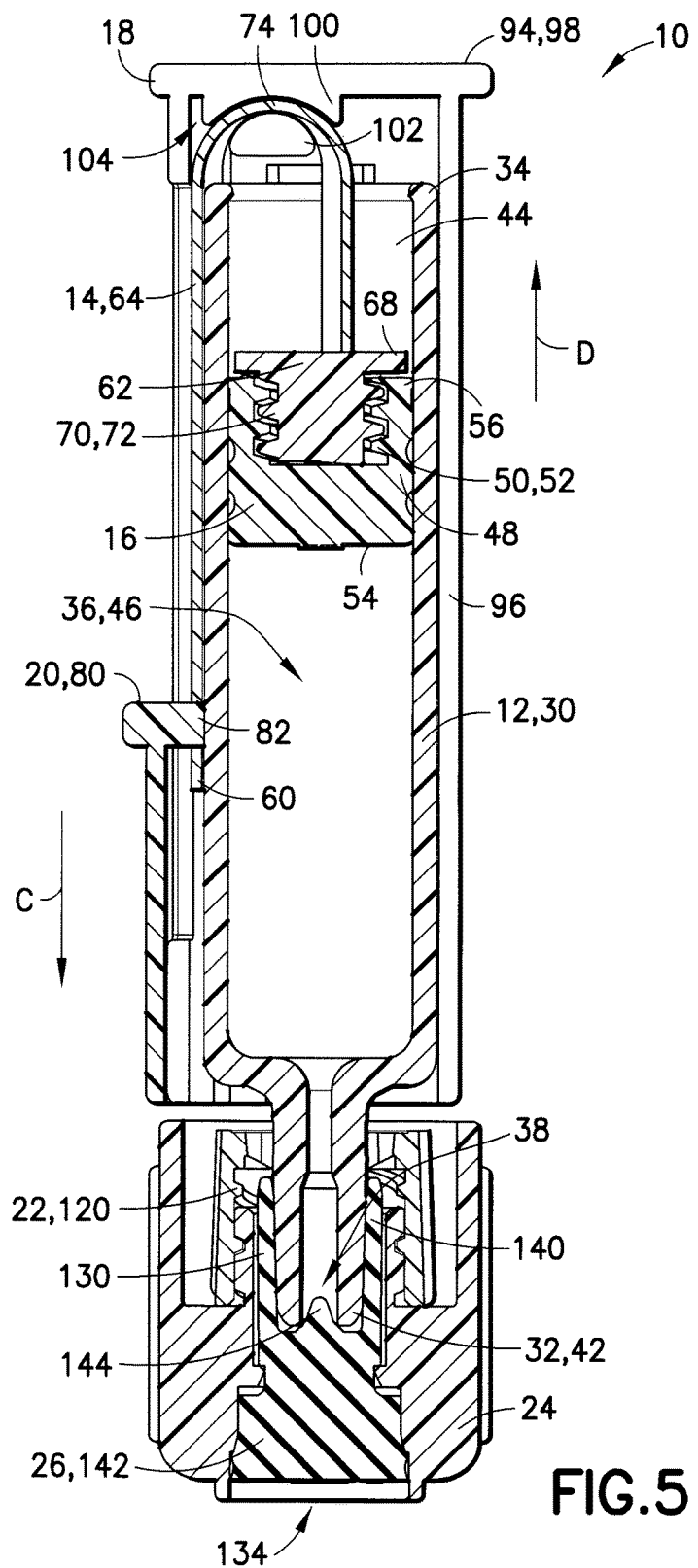
FIG. 5 is a cross-sectional view of the syringe assembly taken along line 5-5 of FIG. 2A in accordance with an embodiment of the present invention.

Referring now to FIGS. 4A, 4B, and 5, the use of syringe assembly 10 to fill syringe barrel 12 with medication from a separate vial prior to use will now be described. With syringe assembly 10 in the position shown in FIGS. 4A and 4B and with a needle assembly locked to distal end 32 of syringe barrel 12 and placed in a vial containing fluid, when it is desired to aspirate or pull the fluid, such as a medication, into distal chamber 46 of syringe barrel 12, a user moves actuator flange 20 in a direction generally along arrow C (FIG. 5) toward distal end 32 of syringe barrel 12 and away from finger pad portion 98 of restraining member 18 until the desired amount of the fluid is pulled into distal chamber 46 of syringe barrel 12. Referring to FIGS. 4B and 5, such movement of actuator flange 20 advances movement of first end 60 of plunger rod 14 in the direction generally along arrow C which actuates movement of second end 62 of plunger rod 14 in a direction generally along arrow D different than the direction generally along arrow C. This is accomplished by flexible portion 74 of plunger rod 14 being received in guide channel 104 and top guide wall 100 and bottom guide wall 102 of restraining member 18 guiding plunger rod 14 in a similar manner as described in detail above regarding expelling a fluid from syringe barrel 12.

In this manner, movement of stopper 16 in the direction generally along arrow D as shown in FIG. 5 creates a vacuum inside distal chamber 46 of syringe barrel 12. As the user moves stopper 16, via plunger rod 14 and actuator flange 20, from the position shown in FIG. 4B to the position shown in FIG. 5, the user actively increases the volume within distal chamber 46 of syringe barrel 12. Because the stopper is sized relative to syringe barrel 12 to provide sealing engagement with the interior wall of syringe barrel 12, as describe above, and because the needle assembly locked to distal end 32 of syringe barrel 12 is placed in a vial containing fluid, no air can enter into distal chamber 46 of syringe barrel 12 and, thus, the same number of air molecules are located within distal chamber 46 as the user actively increases the volume within distal chamber 46. This decreases the pressure in distal chamber 46 of syringe barrel 12 relative to the air pressure outside of syringe barrel 12. Therefore, a vacuum, i.e., a space of lower air pressure, is created to pull the fluid, such as a medication, into distal chamber 46 of syringe barrel 12.

Advantageously, whether syringe assembly 10 is used to collect a fluid into distal chamber 46 of syringe barrel 12 or to expel a fluid out of distal chamber 46 of syringe barrel 12, the length of syringe assembly 10 remains the same during movement between all positions of stopper 16 as shown in FIGS. 2B, 4B, and 5. Accordingly, a syringe assembly of the present disclosure occupies the same amount of space in a filled state and an empty state and syringe assemblies of the present disclosure each have the same length thereby allowing for stacking of these syringes within a storage cabinet in either the filled or empty state.

FIGS. 6A-9 illustrate other exemplary embodiments. The embodiment illustrated in FIGS. 6A-7 includes similar components to the embodiment illustrated in FIGS. 1-5, and the similar components are denoted by a reference number followed by the letter A. The embodiment illustrated in FIGS. 8A-9 also includes similar components to the embodiment illustrated in FIGS. 1-5, and the similar components are denoted by a reference number followed by the letter B. For the sake of brevity, these similar components and the similar steps of using syringe assembly 10A (FIGS. 6A-7) and syringe assembly 10B (FIGS. 8A-9) will not all be discussed in conjunction with the embodiments illustrated in FIGS. 6A-7 and FIGS. 8A-9.

Figure 6A:
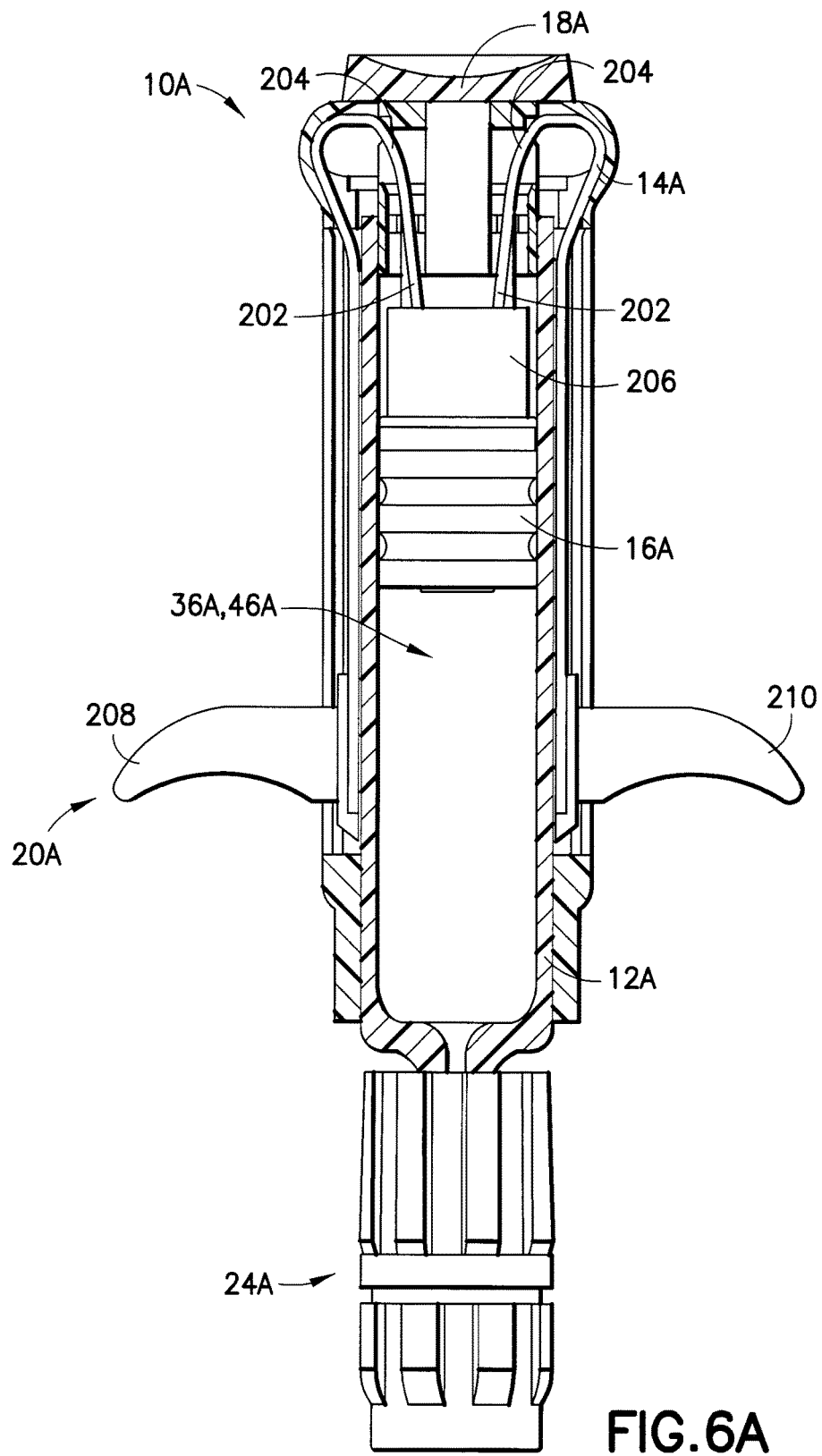
FIG. 6A is a perspective view of a syringe assembly in a first position in accordance with an embodiment of the present invention.
Figure 6B:
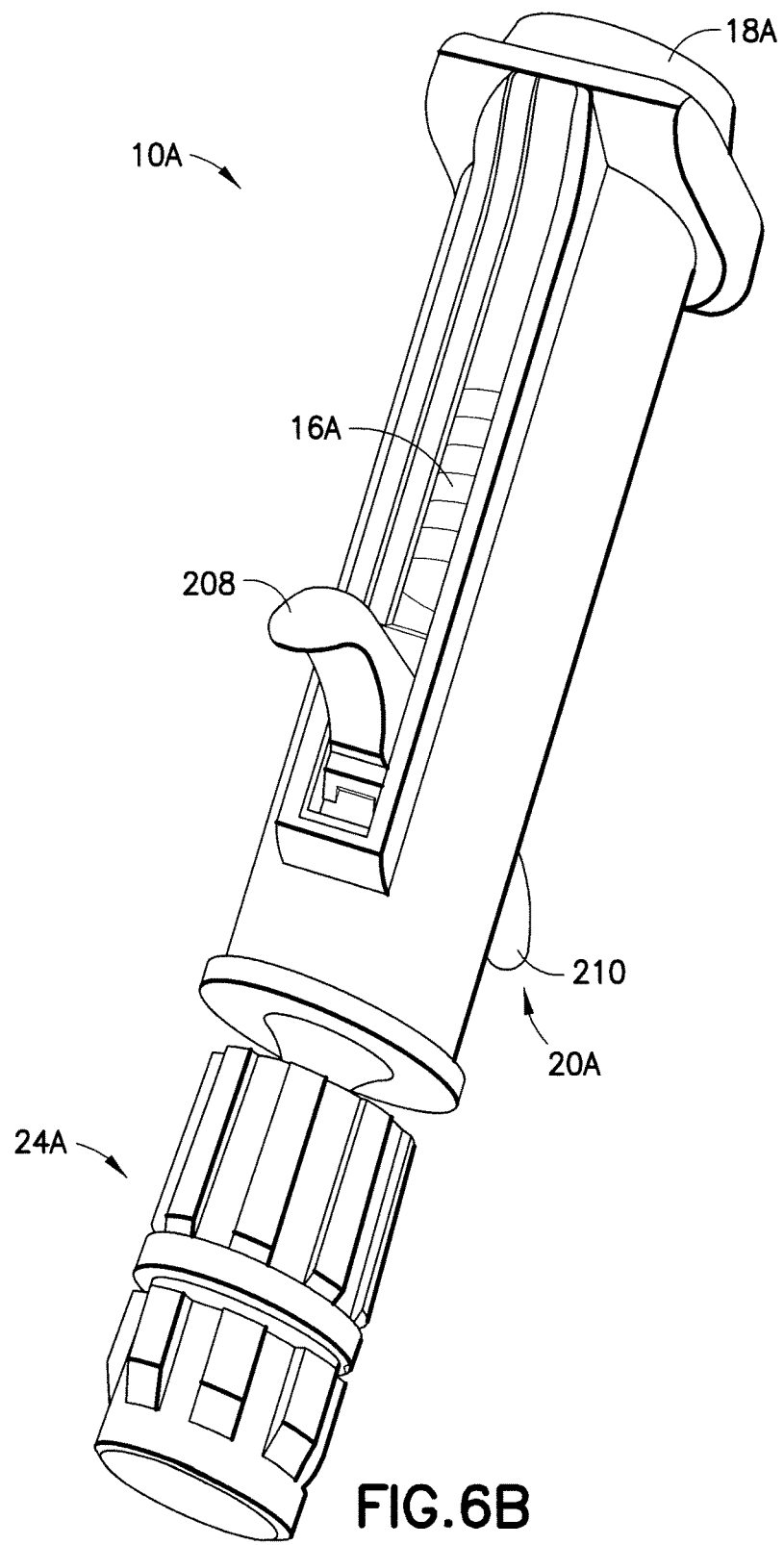
FIG. 6B is a side perspective view of the syringe assembly of FIG. 6A in accordance with an embodiment of the present invention.
Figure 7:
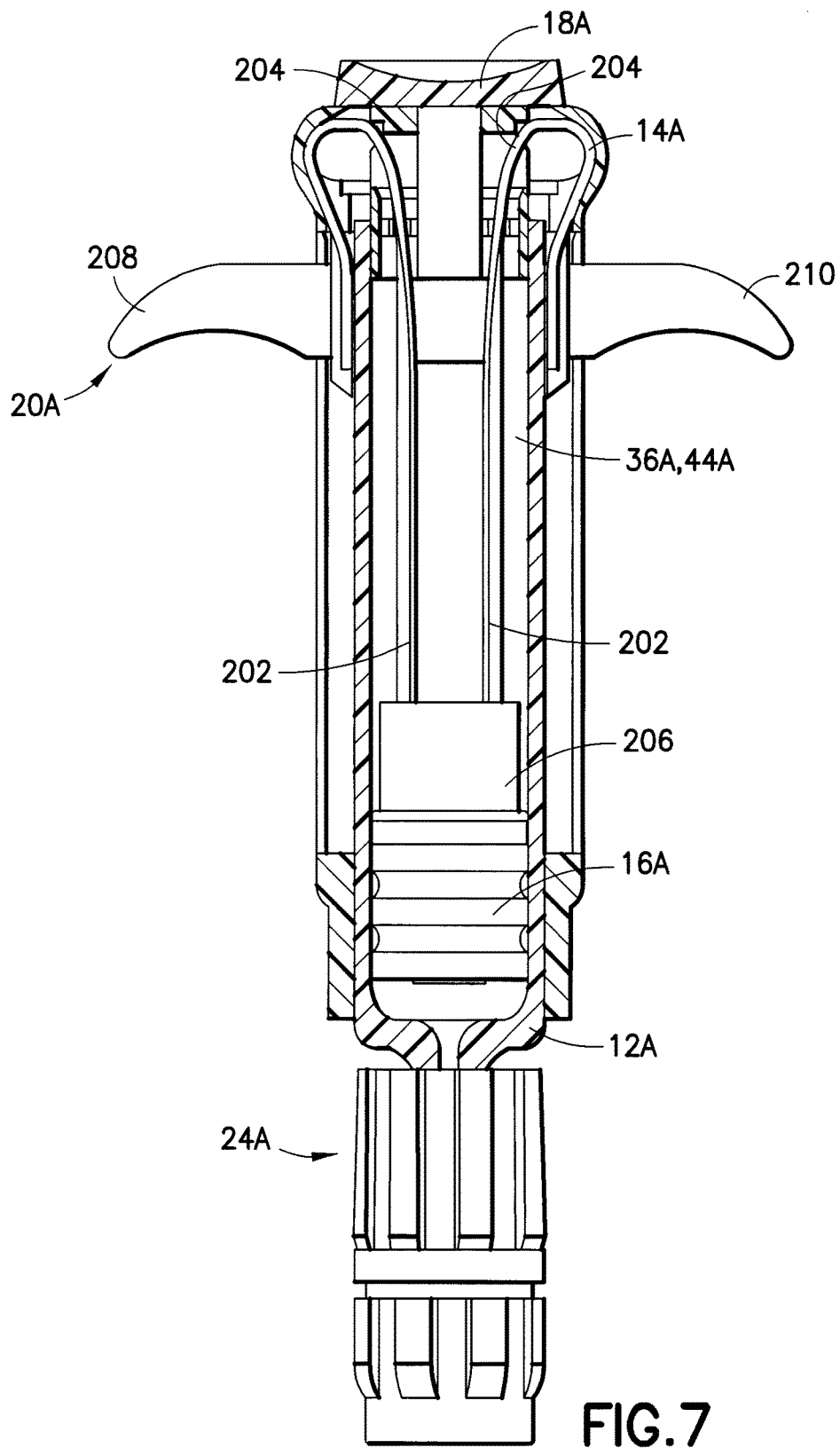
FIG. 7 is a perspective view of the syringe assembly of FIG. 6A in a second position in accordance with an embodiment of the present invention.

Referring to FIGS. 6A-7, plunger rod 14A of syringe assembly 10A includes two opposing rod portions 202 each having a flexible portion 204. Referring to FIGS. 6A and 7, rod portions 202 are disposed on opposing sides of syringe barrel 12A, and each rod portion 202 is secured at one end to a head portion 206 of stopper 16A and at the other end to one of opposing handles 208, 210 of actuator flange 20A.

Figure 8A:
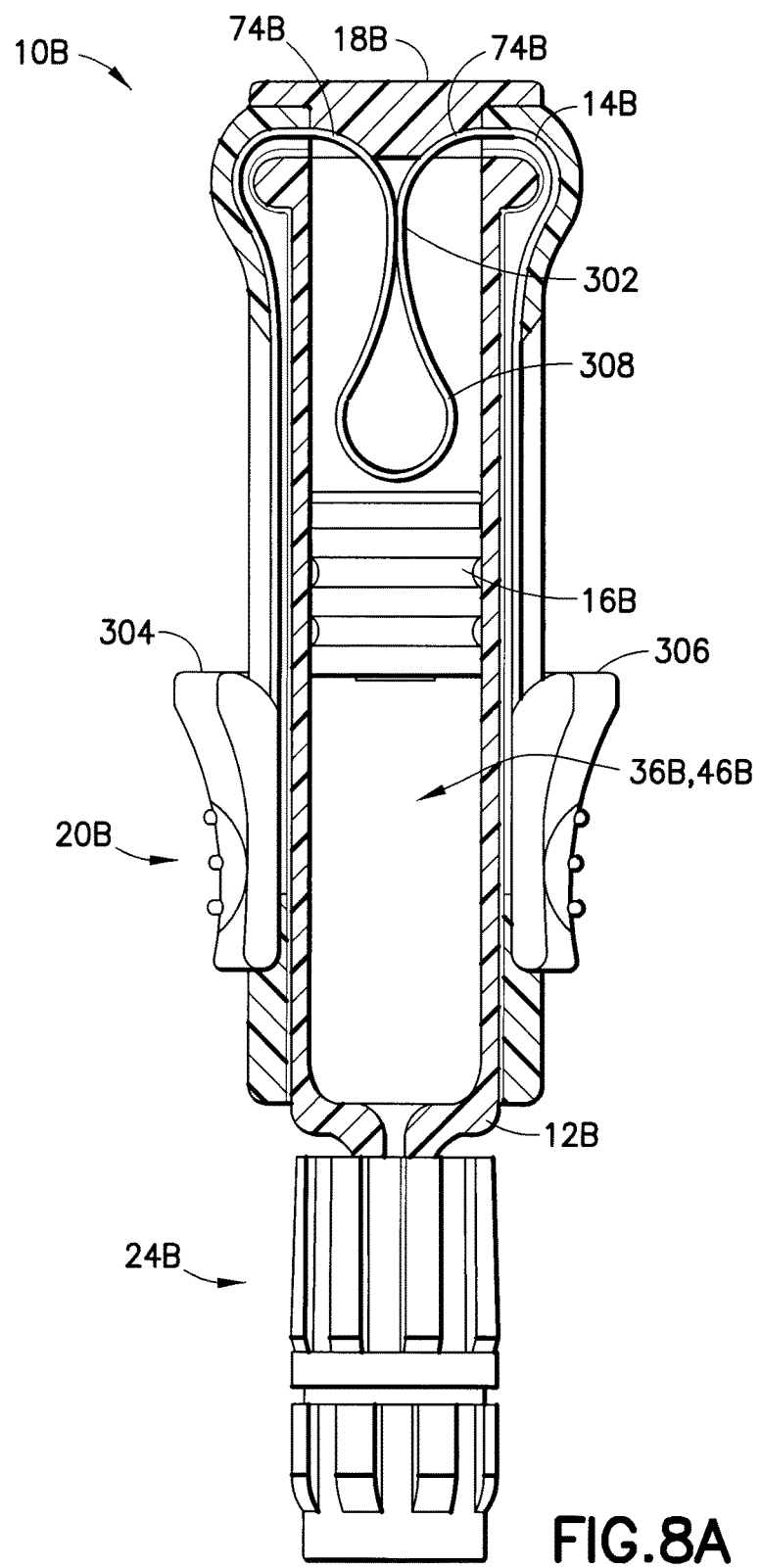
FIG. 8A is a perspective view of a syringe assembly in a first position in accordance with an embodiment of the present invention.
Figure 9:
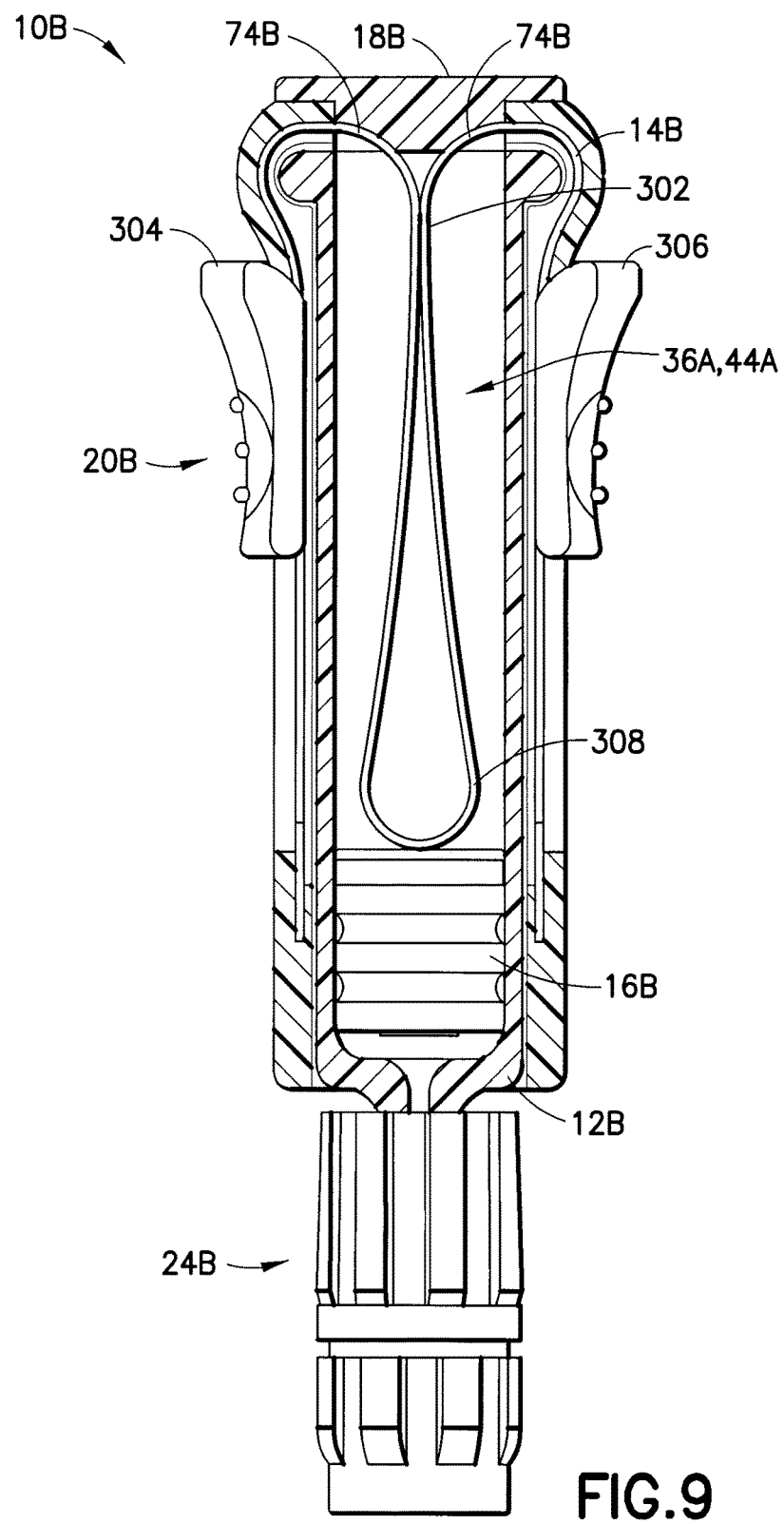
FIG. 9 is a perspective view of the syringe assembly of FIG. 8A in a second position in accordance with an embodiment of the present invention.

In another embodiment, referring to FIGS. 8A-9, plunger rod 14B of syringe assembly 10B includes a continuous rod portion 302 secured at one end to a first portion 304 of actuator flange 20B and at the other end to a second portion 306 of actuator flange 20B. In this embodiment, continuous rod portion 302 forms a looped, head portion 308 that engages stopper 16B, i.e., effective contact between rod portion 302 and stopper 16B, such that movement of rod portion 302 via actuator flange 20B, advances stopper 16B between a first position (FIGS. 8A and 8B) and a second position (FIG. 9).

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A syringe assembly, comprising:
   a syringe barrel having a first end, a second end, and a sidewall extending therebetween and defining a chamber having an interior;
   a stopper slidably disposed within the interior of the chamber of the syringe barrel, the stopper sized relative to the interior of the chamber of the syringe barrel to provide sealing engagement with the sidewall of the syringe barrel;
   a plunger rod having a first end, a second end, and a rod portion extending therebetween, wherein at least a portion of the rod portion is flexible, wherein the second end of the plunger rod is engaged with the stopper such that movement of the first end of the plunger rod in a first direction moves the stopper in a second direction between a first position in which the stopper is located a first distance from the first end of the syringe barrel, and a second position in which the stopper is located a second distance from the first end of the syringe barrel, the second direction being different than the first direction and the second distance being different than the first distance, and wherein the overall length of the syringe assembly is the same when the stopper is in the first position and the second position; and an actuator flange disposed at least partially about the syringe barrel and movable alongside the syringe barrel, the actuator flange being connected to the first end of the plunger rod, the actuator flange including a finger flange for facilitating manual movement of the actuator flange with respect to the syringe barrel in the first direction to advance the first end of the plunger rod in the first direction and the second end of the plunger rod in the second direction.

2. The syringe assembly of claim 1, wherein the plunger rod has a first effective distance in the first position relative to the syringe assembly, and a second effective distance in the second position relative to the syringe assembly, the first effective distance and the second effective distance being equal.

3. The syringe assembly of claim 1, further comprising a fluid contained in the chamber.

4. The syringe assembly of claim 1, wherein the stopper comprises a first engagement portion and the second end of the plunger rod comprises a second engagement portion for securely engaging the first engagement portion.

5. The syringe assembly of claim 1, wherein the stopper comprises a first threaded portion, and the plunger rod comprises a second threaded portion adjacent the second end of the plunger rod, the second threaded portion of the plunger rod threadingly engageable with the first threaded portion of the stopper to secure the plunger rod to the stopper.

6. The syringe assembly of claim 1, wherein the syringe assembly is fully encapsulated by a packaging element.

7. The syringe assembly of claim 1, wherein at least a portion of the syringe assembly is encapsulated by a packaging element.

8. The syringe assembly of claim 7, wherein the packaging element comprises a tear strip.

9. The syringe assembly of claim 1, wherein the actuator flange comprises a projection, and the plunger rod comprises a slot defined therein adjacent the first end of the plunger rod, the slot sized to accept the projection of the actuator flange therein.

10. The syringe assembly of claim 1, wherein the sidewall of the syringe barrel comprises an outer surface, and the actuator flange comprises an inner surface, the actuator flange connected to the plunger rod such that a portion of the plunger rod is slidably restrained between the inner surface of the actuator flange and the outer surface of the syringe barrel.

11. The syringe assembly of claim 1, wherein the rod portion of the plunger rod is formed of an elastomer.

12. The syringe assembly of claim 1, wherein the rod portion of the plunger rod is formed of a flexible metal.

13. The syringe assembly of claim 1, wherein the rod portion of the plunger rod is formed of two or more separate materials.

14. The syringe assembly of claim 13, wherein the separate materials may be one of mechanically attached together, adhesively fixed together, or molded integrally together.

15. A syringe assembly, comprising:
a syringe barrel having a first end, a second end, and a sidewall extending therebetween and defining a chamber having an interior;
a stopper slidably disposed within the interior of the chamber of the syringe barrel, the stopper sized relative to the interior of the chamber of the syringe barrel to provide sealing engagement with the sidewall of the syringe barrel;
a plunger rod having a first end, a second end, and a rod portion extending therebetween, wherein at least a portion of the rod portion is flexible, wherein the second end of the plunger rod is engaged with the stopper;
a finger flange disposed at least partially about the syringe barrel and associated with the first end of the plunger rod and movable with respect to the syringe barrel wherein upon application of a manual force by the application of a squeezing movement between the finger flange and the first end of the syringe barrel causes the stopper to move between a first position in which the stopper is located a first distance from the first end of the syringe barrel, and a second position in which the stopper is located a second distance from the first end of the syringe barrel, the second direction being different than the first direction and the second distance being different than the first distance, and wherein the overall length of the syringe assembly is the same when the stopper is in the first position and the second position; and
wherein at least a portion of the syringe assembly is encapsulated by a packaging element.

16. The syringe assembly of claim 15, wherein the syringe assembly is fully encapsulated by the packaging element.

17. The syringe assembly of claim 15, wherein the packaging element comprises a tear strip.

18. The syringe assembly of claim 17, wherein the tear strip extends longitudinally along the syringe assembly.

19. The syringe assembly of claim 15, further comprising a fluid contained in the chamber.

* * * * *